US007462694B2

(12) United States Patent
Tumer et al.

(10) Patent No.: US 7,462,694 B2
(45) Date of Patent: Dec. 9, 2008

(54) C-TERMINALLY TRUNCATED NON-CYTOTOXIC PAP MUTANTS

(75) Inventors: Nilgun E. Tumer, Belle Mead, NJ (US); Katalin A. Hudak, Toronto (CA); Bijal Parikh, Union, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 229 days.

(21) Appl. No.: 10/467,009

(22) PCT Filed: Feb. 1, 2002

(86) PCT No.: PCT/US02/02792

§ 371 (c)(1),
(2), (4) Date: Jul. 12, 2004

(87) PCT Pub. No.: WO02/062952

PCT Pub. Date: Aug. 15, 2002

(65) Prior Publication Data

US 2004/0241673 A1 Dec. 2, 2004

Related U.S. Application Data

(60) Provisional application No. 60/266,396, filed on Feb. 2, 2001.

(51) Int. Cl.
*A61K 36/00* (2006.01)
*C07K 14/415* (2006.01)

(52) U.S. Cl. ................. 530/370; 530/387.3; 530/391.7; 514/2

(58) Field of Classification Search ....................... None
See application file for complete search history.

(56) References Cited

U.S. PATENT DOCUMENTS 5,756,322 A * 5/1998 Tumer ........................ 530/370

OTHER PUBLICATIONS

Honjo et al. (1997) Bull. Fac. Agr. Saga Univ., vol. 82, pp. 83-90.*

Hudak et al. Generation of pokeweed an tiviral protein mutations in *Saccharomyces cerevisiae*: evidence that ribosome depurination is not sufficient for cytotoxicity. (2004) Nucleic Acids Research, vol. 32, pp. 4244-4256.*

Zhao et al. A pokeweed antiviral protein gene in roots of *Phytolacca americana*. (2005) GenBank Accession AY547315, pp. 1-2.*

Lin et al. Isolation and characterization of a cDNA clone encoding the anti-viral protein from *Phytolacca americana*. (1991) GenBank Accession X55383, pp. 1-2.*

Uckun et al., "TXU (Anti-CD7)-Pokeweed Antiviral Protein As A Potent Inhibitor Of Human Immunodeficiency Virus", Antimicrobial Agents and Chemotherapy, vol. 42, No. 2, pp. 383-388, Feb. 1998.

Erice et al., "Anti-Human Immunodeficiency Virus Type 1 Activity Of An Anti-CD4 Immunoconjugate Containing Pokeweed Antiviral Protein", Antimicrobial Agents and Chemotherapy, vol. 37, No. 4, pp. 835-837, Apr. 1993.

Tumer et al., C-terminal deletion mutant of pokeweed antiviral protein inhibits viral infection but does not depurinate host ribosomes, Proc. Natl. Acad. chi. USA, vol. 94, pp. 3866-3871, Apr. 1997.

Waddick et al., "In Vitro and In Vivo Antileukemic Activity of B43-Pokeweed Antiviral Protein Against Radiation-Resistant Human B-Cell Precursor Leukemia Cells", Blood, vol. 86, No. 11, pp. 4228-4233, Dec. 1, 1995.

Irvin et al., "Pokeweed Antiviral Protein: Ribosome Inactivation And Therapeutic Applications", Pharmacology & Therapeutics, vol. 55, No. 3, pp. 279-302, 1992.

Uckun et al., "Toxicity, biological Activity, and Pharmacokinetics of TXU (Anti-CD7)-Pokeweed Antiviral Protein in Chimpanzees and Adult Patients Infected with Human Immunodeficiency Virus" Journal of Pharmacology & Experimental Therapeutics, vol. 291, No. 3, pp. 1301-1307, 1999.

Hudak et al., "Pokeweed Antiviral Protein Accesses Ribosomes by Binding to L3", Journal of Biological Chemistry, vol. 274, No. 6, pp. 3859-3864, Feb. 5, 1999.

Hudak, et al. "A novel mechanism for inhibition of translation by pokeweed antiviral protein: Depurination of the capped RNA template", RNA, vol. 6, pp. 369-380, 2000.

Schlick et al., "Cytotoxic activity of a recombinant GnRH-PAP fusion toxin on human tumor cell lines", FEBS Letters, vol. 472, No. 2-3, pp. 241-246, 2000.

Ago et al., Eur. J. Biochem. "X-ray structure of a pokeweed antiviral protein, coded by a new genomic clone. at 0.23 nm resolution-a mode 1 structure provides a suitable electrostatic field for substrate binding". 225:369-374 (1994).

Cui et al., "mof4-1 is an allele of the UPF1/IFS2 gene which affects both mRNA turnover and—1 ribosomal frameshifting efficiency". EMBO J. 15:5726-5736 (1996).

Hudak et al., "A C-terminal deletion mutant of pokeweed antiviral protein inhibits programmed +1 ribosomal frameshifting and Ty1 retrotransposition without depurinating the sarcin/ricin loop of rRNA". Virology 279:292-301 (2001).

Hur et al., "Isolation and Characterization of Pokeweed Antiviral Protein Mutations in *Saccharomyces cerevisiae*: Identification of Residues Important for Toxicity". Proc. Natl. Acad. Sci. U.S.A. 92:8448 (1995).

Lodge et al., "Broad-spectrum virus resistance in transgenic plants expressing pokeweed antiviral protein". Proc. Natl. Acad. Sci. U.S.A. 90:7089-7093 (1993).

* cited by examiner

*Primary Examiner*—Cathy Kingdon Worley
(74) *Attorney, Agent, or Firm*—Lerner, David, Littenberg, Krumholz & Mentlik, LLP

(57) ABSTRACT

Disclosed are PAP mutants that are less toxic than wild type PAP and that exhibit depurination activity. Also disclosed are transgenic plants that procedure the PAP mutants, and methods for preparing the plants. Further disclosed are bioconjugates containing the PAP mutants, pharmaceutical compositions containing the bioconjugates, and methods of administering the compositions to treat disease.

5 Claims, 6 Drawing Sheets

SEQUENCE LISTING

```
<160> NUMBER OF SEQ ID NOS: 3

<210> SEQ ID NO 1
<211> LENGTH: 1376
<212> TYPE: DNA
<213> ORGANISM: Phytolacca americana
<220> FEATURE:
<221> NAME/KEY: CDS
<222> LOCATION: (225)..(1160)

<400> SEQUENCE: 1

ctatgaagtc gggtcaaagc atatacaggc tatgcattgt tagaaacatt gatgcctctg     60
```

-continued

```
atcccgataa acaatacaaa ttagacaata agatgacata caagtaccta aactgtgtat    120

gggggagtga aacctcagct gctaaaaaaa cgttgtaaga aaaaaagaaa gttgtgagtt    180

aactacaggg cgaaagtatt ggaactagct agtaggaagg gaag atg aag tcg atg     236
                                                 Met Lys Ser Met
                                                 1

ctt gtg gtg aca ata tca ata tgg ctc att ctt gca cca act tca act      284
Leu Val Val Thr Ile Ser Ile Trp Leu Ile Leu Ala Pro Thr Ser Thr
5                   10                  15                  20

tgg gct gtg aat aca atc atc tac aat gtt gga agt acc acc att agc      332
Trp Ala Val Asn Thr Ile Ile Tyr Asn Val Gly Ser Thr Thr Ile Ser
                25                  30                  35

aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
            40                  45                  50

agt tta aaa tgc tat gga ata cca atg ctg ccc aat aca aat aca aat      428
Ser Leu Lys Cys Tyr Gly Ile Pro Met Leu Pro Asn Thr Asn Thr Asn
        55                  60                  65

cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
    70                  75                  80

aca cta atg ctg aga cga aac aat ttg tat gtg atg ggt tat tct gat      524
Thr Leu Met Leu Arg Arg Asn Asn Leu Tyr Val Met Gly Tyr Ser Asp
85                  90                  95                  100

ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115

ggt act gaa cgc caa gat gta gag act act ctt tgc cca gcc aat tct      620
Gly Thr Glu Arg Gln Asp Val Glu Thr Thr Leu Cys Pro Ala Asn Ser
            120                 125                 130

cgt gtt agt aaa aac ata aac ttt gat agt cga tat cca aca ttg gaa      668
Arg Val Ser Lys Asn Ile Asn Phe Asp Ser Arg Tyr Pro Thr Leu Glu
        135                 140                 145

tca aaa gcg gga gta aaa tca aga agt cag gtc caa ctg gga att caa      716
Ser Lys Ala Gly Val Lys Ser Arg Ser Gln Val Gln Leu Gly Ile Gln
    150                 155                 160

ata ctc gac agt aat att gga aag att tct gga gtg atg tca ttc act      764
Ile Leu Asp Ser Asn Ile Gly Lys Ile Ser Gly Val Met Ser Phe Thr
165                 170                 175                 180

gag aaa acc gaa gcc gaa ttc cta ttg gta gcc ata caa atg gta tca      812
Glu Lys Thr Glu Ala Glu Phe Leu Leu Val Ala Ile Gln Met Val Ser
                185                 190                 195

gag gca gca aga ttc aag tac ata gag aat cag gtg aaa act aat ttt      860
Glu Ala Ala Arg Phe Lys Tyr Ile Glu Asn Gln Val Lys Thr Asn Phe
            200                 205                 210

aac aga gca ttc aac cct aat ccc aaa gta ctt aat ttg caa gag aca      908
Asn Arg Ala Phe Asn Pro Asn Pro Lys Val Leu Asn Leu Gln Glu Thr
        215                 220                 225

tgg ggt aag att tca aca gca att cat gat gcc aag aat gga gtt tta      956
Trp Gly Lys Ile Ser Thr Ala Ile His Asp Ala Lys Asn Gly Val Leu
    230                 235                 240

ccc aaa cct ctc gag cta gtg gat gcc agt ggt gcc aag tgg ata gtg     1004
Pro Lys Pro Leu Glu Leu Val Asp Ala Ser Gly Ala Lys Trp Ile Val
245                 250                 255                 260

ttg aga gtg gat gaa atc aag cct gat gta gca ctc tta aac tac gtt     1052
Leu Arg Val Asp Glu Ile Lys Pro Asp Val Ala Leu Leu Asn Tyr Val
                265                 270                 275

ggt ggg agc tgt cag aca act tat aac caa aat gcc atg ttt cct caa     1100
Gly Gly Ser Cys Gln Thr Thr Tyr Asn Gln Asn Ala Met Phe Pro Gln
```

-continued

```
            280                 285                 290

ctt ata atg tct act tat tat aat tac atg gtt aat ctt ggt gat cta      1148
Leu Ile Met Ser Thr Tyr Tyr Asn Tyr Met Val Asn Leu Gly Asp Leu
        295                 300                 305

ttt gaa gga ttc tgatcataaa cataataagg agtatatata tattactcca          1200
Phe Glu Gly Phe
    310

actatattat aaagcttaaa taagaggccg tgttaattag tacttgttgc cttttgcttt   1260

atggtgttgt ttattatgcc ttgtatgctt gtaatattat ctagagaaca agatgtactg   1320

tgtaatagtc ttgtttgaaa taaaacttcc aattatgatg caaaaaaaaa aaaaaa       1376


<210> SEQ ID NO 2
<211> LENGTH: 312
<212> TYPE: PRT
<213> ORGANISM: Phytolacca americana

<400> SEQUENCE: 2

Met Lys Ser Met Leu Val Val Thr Ile Ser Ile Trp Leu Ile Leu Ala
  1               5                  10                  15

Pro Thr Ser Thr Trp Ala Val Asn Thr Ile Ile Tyr Asn Val Gly Ser
             20                  25                  30

Thr Thr Ile Ser Lys Tyr Ala Thr Phe Leu Asn Asp Leu Arg Asn Glu
         35                  40                  45

Ala Lys Asp Pro Ser Leu Lys Cys Tyr Gly Ile Pro Met Leu Pro Asn
     50                  55                  60

Thr Asn Thr Asn Pro Lys Tyr Val Leu Val Glu Leu Gln Gly Ser Asn
 65                  70                  75                  80

Lys Lys Thr Ile Thr Leu Met Leu Arg Arg Asn Asn Leu Tyr Val Met
                 85                  90                  95

Gly Tyr Ser Asp Pro Phe Glu Thr Asn Lys Cys Arg Tyr His Ile Phe
            100                 105                 110

Asn Asp Ile Ser Gly Thr Glu Arg Gln Asp Val Glu Thr Thr Leu Cys
        115                 120                 125

Pro Ala Asn Ser Arg Val Ser Lys Asn Ile Asn Phe Asp Ser Arg Tyr
    130                 135                 140

Pro Thr Leu Glu Ser Lys Ala Gly Val Lys Ser Arg Ser Gln Val Gln
145                 150                 155                 160

Leu Gly Ile Gln Ile Leu Asp Ser Asn Ile Gly Lys Ile Ser Gly Val
                165                 170                 175

Met Ser Phe Thr Glu Lys Thr Glu Ala Glu Phe Leu Leu Val Ala Ile
            180                 185                 190

Gln Met Val Ser Glu Ala Ala Arg Phe Lys Tyr Ile Glu Asn Gln Val
        195                 200                 205

Lys Thr Asn Phe Asn Arg Ala Phe Asn Pro Asn Pro Lys Val Leu Asn
    210                 215                 220

Leu Gln Glu Thr Trp Gly Lys Ile Ser Thr Ala Ile His Asp Ala Lys
225                 230                 235                 240

Asn Gly Val Leu Pro Lys Pro Leu Glu Leu Val Asp Ala Ser Gly Ala
                245                 250                 255

Lys Trp Ile Val Leu Arg Val Asp Glu Ile Lys Pro Asp Val Ala Leu
            260                 265                 270

Leu Asn Tyr Val Gly Gly Ser Cys Gln Thr Thr Tyr Asn Gln Asn Ala
        275                 280                 285
```

-continued

```
Met Phe Pro Gln Leu Ile Met Ser Thr Tyr Tyr Asn Tyr Met Val Asn
    290                 295                 300

Leu Gly Asp Leu Phe Glu Gly Phe
305                 310


<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3

ggcgttcagc cataatcc                                                   18
```

C-TERMINALLY TRUNCATED NON-CYTOTOXIC PAP MUTANTS

PRIORITY

This application claims priority on the basis of U.S. provisional application No. 60/266,396, filed Feb. 2, 2001.

STATEMENT REGARDING FEDERALLY SPONSORED RESEARCH

The invention was supported by NSF grant MCB99-82498. Thus, the Government may have rights in the invention.

BACKGROUND OF THE INVENTION

The invention relates to pokeweed antiviral protein and expression of nucleic acids encoding various PAP mutants in transgenic plants. Many commercially valuable agricultural crops are prone to infection by plant viruses. These viruses are capable of inflicting significant damage to a crop in a given season, and thus can drastically reduce its economic value. The reduction in economic value to the farmer in turn results in a higher cost of goods to ultimate purchasers. Several published studies have been directed to the expression of plant virus capsid proteins in a plant in an effort to confer resistance to viruses. See, e.g., Abel et al., Science 232:738-743 (1986); Cuozzo et al., Bio/Technology 6:549-557 (1988); Hemenway et al., EMBO J. 7:1273-1280 (1988); Stark et al., Bio/Technology 7:1257-1262 (1989); and Lawson et al., Bio/Technology 8:127-134 (1990). The transgenic plants exhibited resistance only to the homologous virus and related viruses, however, and not to unrelated viruses. Kawchuk et al., Mol. Plant-Microbe Interactions 3(5):301-307 (1990), disclose the expression of wild-type potato leafroll virus (PLRV) coat protein gene in potato plants. Although the infected plants exhibited resistance to PLRV, all of the transgenic plants that were inoculated with PLRV became infected with the virus and thus allowed for the continued transmission of the virus such that high levels of resistance could not be expected. See U.S. Pat. No. 5,304,730.

Pokeweed antiviral protein (PAP) is a 29-kDa Type I ribosome-inhibiting protein (RIP) found in the cell walls of *Phytolacca americana* (pokeweed). See, Wang et al., Adv. Virus Res. 55:325-356 (2000). It is a single polypeptide chain that catalytically removes a specific adenine residue from a highly conserved stem-loop structure (i.e., the α-sarcin loop) in the 28S rRNA of eukaryotic ribosomes, thus interfering with Elongation Factor-2 binding and blocking cellular protein synthesis. More specifically, PAP removes an adenine base by cleavage of the N-glycosidic bond at $A^{4324}$ in rat 28 S rRNA and at homologous sites on ribosomes from other organisms. See, e.g. Irvin et al., Pharmac. Ther. 55:279-302 (1992); Endo et al., Biophys. Res. Comm. 150:1032-1036 (1988); and Hartley et al., FEBS Lett. 290:65-68 (1991). PAP recognizes and binds to the ribosomal protein L3 that is essential for subsequent depurination of the α-sarcin loop. See, Hudak et al., J. Biol. Chem. 274:3859-3864 (1999).

PAP protein confers resistance to a broad spectrum of viruses when expressed in crop plants, yeast and cultured human cells. Lodge et al., Proc. Natl. Acad. Sci. USA 90:7089-7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile. Since that time, Applicant has found that various PAP mutants provide comparable resistance to plant pests such as viruses and fungi but are less toxic than wild-type PAP. See, U.S. Pat. Nos. 5,756,322; 5,880,329 and 6,137,030. The PAP mutants disclosed in the prior art that exhibited less cytotoxicity (e.g., phytotoxicity) than wild-type PAP also exhibited the capability of depurinating the cell ribosomes. The belief was that cytotoxic effect was a result of translation inhibition due to depurinated rRNA.

SUMMARY OF THE INVENTION

Applicants have discovered that PAP depurination can occur in the absence of cytotoxicity and that both events are independent. That is, just because a PAP protein depurinates a ribosome and thus can effectively interfere with the ability of a cell to manufacture proteins does not mean the PAP protein will also be cytotoxic.

One aspect of the present invention is directed to PAP mutants that depurinate the ribosomes of the cell, but are less toxic to cells than wild type PAP. The Pokeweed Antiviral Protein (PAP) mutant is said to be substantially non-toxic and exhibits ribosome depurination activity. One preferred PAP mutant differs from wild-type PAP in that the native tyrosine residue at position 123 is replaced by alanine (hereinafter PAP (1-262, Y123A)). Other preferred PAP mutants contain PAP (1-262, S14M, Y16A), PAP (1-262, L71R), PAP (1-262, V73E), PAP (1-262, M74R), PAP (1-262, Y76A) and PAP (1-262, Y1231). Yet other preferred PAP mutants differ from wild-type PAP substantially in that they are truncated at their C-termini from 10 to 20 mature PAP amino acids. These PAP mutants are designated PAP (1-242), PAP (1-243), PAP (1-244), PAP (1-245), PAP (1-246), PAP (1-247), PAP (1-248), PAP (1-249), PAP (1-250) and PAP (1-251). DNAs encoding the PAP mutants, chimeric constructs thereof, including vectors and non-human hosts transformed with the constructs, are also provided.

Another aspect of the present invention is directed to transgenic plants that express nucleic acids encoding the PAP mutants. The plants exhibit resistance to a broad spectrum of plant pests such as viruses and fungi. The invention also provides plant parts e.g., leaves, stems and shoots, as well as plant cells and protoplasts, containing a DNA molecule encoding a PAP mutant, from which whole plants expressing the DNA are generated. The invention applies to flowering plants in general, including both monocots and dicots. In preferred embodiments, the plants are corn, rice, wheat, turfgrass, soybean, cotton canola, potato, tomato and cucurbits. Seed derived from the transgenic plants is also provided. Methods of making the transgenic plants are further provided.

The PAP mutants of the present invention also have utility as biotherapeutic agents. Thus, a further aspect of the present invention is directed to a fusion protein or an immunoconjugate containing the PAP mutant and a targeting moiety that binds a receptor on or in a cell. The targeting moiety is a ligand that specifically targets to infected, diseased or otherwise unwanted cells. Thus, methods of treating mammals e.g., humans, suffering from diseases characterized by the presence and/or abnormal growth of such cells are also provided. In preferred embodiments, the agent is designed to target cells infected with a virus, or a cancer cell. DNAs encoding the fusion proteins, and constructs containing the DNAs, therapeutic compositions containing the fusion proteins or immunoconjugates, and methods of using same e.g., to treat cancer or AIDS patients, are also provided.

BEST MODE OF CARRYING OUT THE INVENTION

Figure 1:
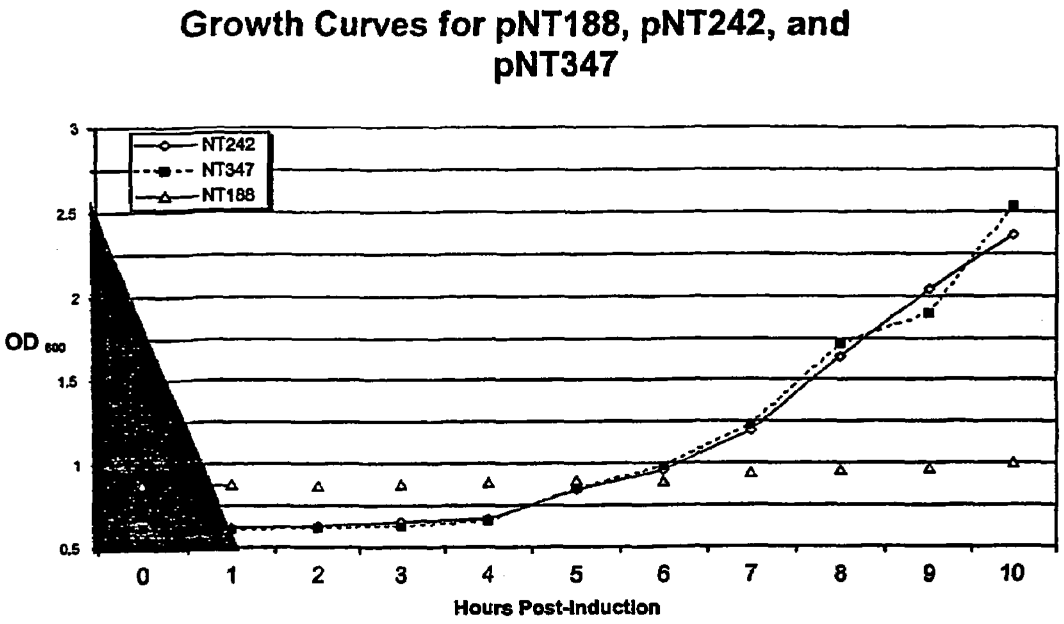
FIG. 1 is a graph showing growth of yeast cells that express wild-type PAP (PAPwt) or PAP mutants of the present invention.

By "wild-type PAP," it is meant the PAP amino acid sequence 1-262, the 22-amino acid N-terminal signal peptide ("the N-terminal signal sequence of wild-type PAP"), and the 29 amino acid C-terminal extension (amino acids enumerated 263-291), set forth below as SEQ ID NO:2. The corresponding nucleotide sequence is set forth as SEQ ID NO:1. Thus, by the terms "wild-type, mature PAP," or "mature PAP", it is meant the PAP amino acid sequence 1-262.

```
5'CTATGAAGTCGGGTCAAAGCATATACAGGCTATGCATTGTTAGAAACATTGAT

GCCTCTGATCCCGATAAACAATACAAATTAGACAATAAGATGACATACAAGTAC

CTAAACTGTGTATGGGGGAGTGAAACCTCAGCTGCTAAAAAAACGTTGTAAGAA

AAAAAGAAAGTTGTGAGTTAACTACAGGGCGAAAGTATTGGAACT

AGCTAGTAGGAAGGGAAG ATG AAG TCG ATG CTT GTG GTG ACA ATA TCA

ATA

                   Met Lys Ser Met Leu Val Val Thr Ile Ser Ile
                                         (67)

TGG CTC ATT CTT GCA CCA ACT TCA ACT TGG GCT GTG AAT ACA ATC ATC TAC

Trp Leu Ile Leu Ala Pro Thr Ser Thr Trp Ala Val Asn Thr Ile Ile Tyr
                                            (1)

               (100)

AAT GTT GGA AGT ACC ACC ATT AGC AAA TAC GCC AGT TTT CTG AAT GAT CTT

Asn Val Gly Ser Thr Thr Ile Ser Lys Tyr Ala Thr Phe Leu Asn Asp Leu
            (10)                                (20)

CGT AAT GAA GCG AAA GAT CCA AGT TTA AAA TGC TAT GGA ATA CCA ATG CTG

Arg Asn Glu Ala Lys Asp Pro Ser Leu Lys Cys Tyr Gly Ile Pro Met Leu
                    (30)                                        (40)

CCC AAT ACA AAT ACA AAT CCA AAG TAC GTG TTG GTT GAG CTC CAA GGT TCA

Pro Asn Thr Asn Thr Asn Pro Lys Tyr Val Leu Val Glu Leu Gln Gly Ser
                                (50)

AAT AAA AAA ACC ATC ACA CTA ATG CTG AGA CGA AAC AAT TTG TAT GTG ATG

Asn Lys Lys Thr Ile Thr Leu Met Leu Arg Arg Asn Asn Leu Tyr Val Met
        (60)                                (70)

GGT TAT TCT GAT CCC TTT GAA ACC AAT AAA TGT CGT TAC CAT ATC TTT AAT

Gly Tyr Ser Asp Pro Phe Glu Thr Asn Lys Cys Arg Tyr His Ile Phe Asn
                    (80)                                (90)

GAT ATC TCA GGT ACT GAA CGC CAA GAT GTA GAG ACT ACT CTT TGC CCA AAT
```

-continued

```
Asp Ile Ser Gly Thr Glu Arg Gln Asp Val Glu Thr Thr Leu Cys Pro Asn
                            (100)

GCC AAT TCT CGT GTT AGT AAA AAC ATA AAC TTT GAT AGT CGA TAT CCA ACA

Ala Asn Ser Arg Val Ser Lys Asn Ile Asn Phe Asp Ser Arg Tyr Pro Thr
    (110)                               (120)

TTG GAA TCA AAA GCG GGA GTA AAA TCA AGA AGT CAG GTC CAA CTG GGA ATT

Leu Glu Ser Lys Ala Gly Val Lys Ser Arg Ser Gln Val Gln Leu Gly Ile
                (130)                                   (140)

CAA ATA CTC GAC AGT AAT ATT GGA AAG ATT TCT GGA GTG ATG TCA TTC ACT

Gln Ile Leu Asp Ser Asn Ile Gly Lys Ile Ser Gly Val Met Ser Phe Thr
                        (150)

GAG AAA ACC GAA GCC GAA TTC CTA TTG GTA GCC ATA CAA ATG GTA TCA GAG

Glu Lys Thr Glu Ala Glu Phe Leu Leu Val Ala Ile Gln Met Val Ser Glu
(160)                               (170)

GCA GCA AGA TTC AAG TAC ATA GAG AAT CAG GTG AAA ACT AAT TTT AAC AGA

Ala Ala Arg Phe Lys Tyr Ile Glu Asn Gln Val Lys Thr Asn Phe Asn Arg
            (180)                                   (190)

GCA TTC AAC CCT AAT CCC AAA GTA CTT AAT TTG CAA GAG AGA TGG GGT AAG

Ala Phe Asn Pro Asn Pro Lys Val Leu Asn Leu Gln Glu Thr Trp Gly Lys
                        (200)                           (210)

ATT TCA ACA GCA ATT CAT GAT GCC AAG AAT GGA GTT TTA CCC AAA CCT CTC

Ile Ser Thr Ala Ile His Asp Ala Lys Asn Gly Val Leu Pro Lys Pro Leu
                                (220)

GAG CTA GTG GAT GCC AGT GGT GCC AAG TGG ATA GTG TTG AGA GTG GAT GAA

Glu Leu Val Asp Ala Ser Gly Ala Lys Trp Ile Val Leu Arg Val Asp Glu
        (230)                                   (240)

ATC AAG CCT GAT GTA GCA CTC TTA AAC TAC GTT GGT GGG AGC TGT CAG ACA

Ile Lys Pro Asp Val Ala Leu Leu Asn Tyr Val Gly Gly Ser Cys Gln Thr
                    (250)                               (260)

ACT TAT AAC CAA AAT GCC ATG TTT CCT CAA CTT ATA ATG TCT ACT TAT TAT

Thr Tyr Asn Gln Asn Ala Met Phe Pro Gln Leu Ile Met Ser Thr Tyr Tyr
(262)                       (270)

AAT TAC ATG GTT AAT CTT GGT GAT CTA TTT GAA GGA TTC TGATCATAAACA

Asn Tyr Met Val Asn Leu Gly Asp Leu Phe Glu Gly Phe
    (280)                               (290)

TAATAAGGAGTATATATATATTACTCCAACTATATTATAAAGCTTAAATAAGAGG

CCGTGTTAATTAGTACTTGTTGCCTTTTGCTTTATGGTGTTGTTTATTATGCCTTGT

ATGCTTGTAATATTATCTAGAGAACAAGATGTACTGTGTAATAGTCTTGTTTGAA

ATAAAACTTCCAATTATGATGCAAAAAAAAAAAAAAA3'
```

The sequences contain 5' and 3' non-coding, flanking sequences. Upon expression in eukaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263-292)"), yielding mature, wild-type PAP (hereinafter "PAP (1-262)") (i.e., that which is isolated from *Phytolacca americana* leaves), having a molecular weight of about 29 kD. See Irvin et al., Pharmac. Ther. 55:279-302 (1992); Dore et al., Nuc. Acids Res. 21(18): 4200-05 (1993); Monzingo et al., J. Mol. Biol. 233:705-15 (1993); and Turner et al., Proc. Natl. Acad. Sci. USA 92:8448-52 (1995). PAP has been further characterized in terms of three distinct domains, namely the N-terminal domain which includes amino acid residues 1-69, a central domain which includes amino acid residues 70-179 and a C-terminal domain which includes amino acid residues 180-262. The PAP mutants embraced by the present invention include N-terminal domain mutants, central domain mutants and C-terminal domain mutants.

The terms "depurination", "depurination activity" or "depurination catalytic activity" are used interchangeably herein. These terms are not interpreted so as to require depurination of adeninyl residues from ribosomal RNA at the same rate and/or to the same extent as achieved by wild-type PAP. For example, the extent of depurination may be comparable to or even exceed that of wild-type PAP over a given time period. Differences in the rate and/or extent of depurination activity of preferred PAP mutants of the present invention compared to wild-type PAP are graphically illustrated in FIGS. 2B, 2C and 4. On the other hand, the depurination activity is non-negligible. An example of a PAP mutant that exhibits negligible depurination activity is the active site PAP mutant E176V. Methods for measuring depurination activity involving primer extension are described in the examples. Another method suitable for this purpose involves an RNase protection assay. RNA is isolated from the cell that expresses the given PAP mutant in accordance with standard techniques. It is cleaved at the site of depurination (e.g., such as by treatment with aniline). An RNase protection probe is designed, based on nucleotides that flank the depurination site. To synthesize the probe, forward and reverse primers complementary to rRNA sequences that flank the depurination site may be prepared, which in turn will generate a PCR product using cellular (e.g., yeast) RNA as a template. One of the primers contains a promoter (e.g., phage T7 polymerase promoter) such that it is incorporated into the PCR product The product is then used in an RNase protection assay (preferably as described in Tumer et al., J. Virol. 72:1036-1042 (1998)). Once the depurinated rRNA is cleaved, the probe will yield protected fragments of different sizes, which can be visualized on a sequencing gel.

The PAP mutants of the present invention are less cytotoxic than wild-type PAP. By less cytotoxic or toxic, it is meant that the PAP mutants do not significantly inhibit cell growth like wild type PAP but in any event do not significantly affect cell viability. This determination can be made in accordance with a combination of standard techniques, illustrations of which are set forth in the examples. First, a determination is made as to whether the PAP mutant inhibits cell growth as compared to wild type PAP. One method involves growing cells such as yeast that produce the PAP mutant in question and plating and re-plating the cells on selective media. Another method involves measuring doubling time of growth of the cells in selective media after the induction of PAP production. As can be seen from example 4 (and the results shown in table 3), PAP mutants exhibiting doubling times approximating the doubling time for wild type PAP tended to be toxic and thus outside the scope of the present invention. PAP mutants that caused doubling times of cells approximately PAPx (the active site mutant, E176V), tended to be nontoxic. The second step involves a determination of whether the PAP mutant causes cell death. In this case, a viability assay will distinguish between PAP mutants that cause cell death and that are toxic versus PAP mutants that might appear to be toxic (on account of having a doubling time approximately that for wild type PAP) but actually do not cause cell death, and thus are considered to be nontoxic. There are also unusual situations in which a PAP mutant appears to be nontoxic based on its effect on cell growth but is still toxic. (See table 3 and comparative data for S14M versus S14M, Y16A.) These phenomena may be explained by the fact that inhibition of cell growth does not always correlate with cell viability. Thus, regardless of whether the PAP mutants of the present invention have a significant effect on doubling time of cells, their effect on cell viability is significantly less than that of wild-type PAP.

Rajamohan et al., J. Biol. Chem. 275(5):3382-90 (2000), report a PAP mutant having a double alanine substitution at residues 122 and 123 (i.e., R122A, Y123A, in Applicants' nomenclature) resulted in nearly complete loss (i.e., greater than 1700-fold less active) of ribosomal depurination activity. The working hypothesis is that Y123 is an active site residue and thus plays an important role in catalytic deadenylation. In direct contrast to these results, one of Applicants' preferred embodiments, a PAP mutant containing an active site substitution at position Y123, i.e., PAP (1-262, Y123A), exhibits depurination activity similar to that of wild-type PAP. As shown in example 1, by 8 hours post induction, similar levels of depurination were observed in the wild-type PAP and in the Y123A mutant PAP (NT242). The alanine residue at position 123 of a preferred PAP mutant is a more preferred substitution; it is not critical. That is, other substitutions e.g., conservative substitutions with other neutral amino acids, i.e., glycine, valine, isoleucine, leucine, proline and methionine can be made. Other preferred PAP mutants contain PAP (1-262, S14M, Y16A), PAP (1-262, L71R), PAP (1-262, V73E), PAP (1-262, M74R), PAP (1-262, Y76A) and PAP (1-262, Y123I). In the case of the single substitution mutants, other amino acid residues can be substituted, preferably in a conservative manner, provided that the requisite properties are maintained. In the case of the double substitution mutant, the S14M mutation is important but amino acid residues other than alanine may be substituted for Y at position 16 provided once again, that the requisite properties are maintained.

Yet other preferred PAP mutants differ from wild-type PAP substantially in that they are truncated at their C-termini from 10 to 20 mature PAP amino acids. These PAP mutants are designated PAP (1-242), PAP (1-243), PAP (1-244), PAP (1-245), PAP (1-246), PAP (1-247), PAP (1-248), PAP (1-249), PAP (1-250), PAP (1-251) and PAP (1-252).

Yet other PAP mutants of the present invention may be identified by random mutagenesis of PAP-encoding nucleic acids, expression of the mutagenized nucleic acids in cells, and testing the mutants for depurination and toxicity. Preferred cells in which to identify non-toxic PAP mutants are yeast cells. Once non-toxic, depurinating PAP mutants are identified, the nucleic acids may be sequenced.

Expression of the PAP mutants of the present invention in a transgenic plant confers broad spectrum virus resistance, i.e., resistance to or the capability of suppressing infection by a number of unrelated viruses, including but not limited to RNA viruses e.g. potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge et al., supra., Tomlinson et al., J. Gen. Virol. 22:225-32 (1974); and Chen et al., Plant Pathol. 40:612-20 (1991).

Expression of the PAP mutants in plants also confers resistance to a broad spectrum of fungi that infect plants. There is increased resistance to diseases caused by plant fungi, including those caused by *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Fusarium* (causing root rot of bean, dry rot of potatoes), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Schlerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Gloinerella, Colletotrichum, Helminthosporium, Alterneria, Botrytis, Cladosporium* and *Aspergillus*. Applicant also believes that the PAP mutants confer increased resistance to insects, bacteria and nematodes in plants. Important bacterial diseases to which the PAP mutants impart increased resistance include those caused by *Pseudomonas, Xanthomonas, Erwinia, Clavibacter* and *Streptomyces*.

DNAs encoding the PAP mutants can be made in accordance with standard techniques. See Ausubel et al. (eds.), Vol. 1, Chap. 8 in *Current Protocols in Molecular Biology*, Wiley, N.Y. (1990). The DNAs may also be prepared via PCR techniques. See PCR Protocols, Innis et al. (eds.), Academic Press, San Diego, Calif. (1990). Referring back to the amino acid and corresponding nucleotide sequences of wild type PAP, for example, the codon changes at the nucleotide level for the aforementioned N-terminal domain and central domain mutants are as follows: PAP (1-262, S14M, Y16A) (codon for S, AGC, changed to ATG, and the codon for Y, TAC, changed to GCC); PAP (1-262, L71R) (codon for L, TTG, changed to CGG); PAP (1-262, V73#) (codon for V, GTG, changed to GAG); PAP (1-262, M74R) (codon for M, ATG, changed to CGG); PAP (1-262, Y76A) (codon for Y, TAT, changed to GCT); PAP (1-262, Y123A) (codon for Y, TAT, changed to GCT); and PAP (1-22, Y123I) (codon for Y, TAT, changed to ATT). The PAP DNA (e.g., a cDNA) is preferably inserted into a plant transformation vector in the form of an expression cassette containing all of the necessary elements for transformation of plant cells. The expression cassette typically contains, in proper reading frame, a promoter functional in plant cells, a 5' non-translated leader sequence, the mutant PAP DNA, and a 3' non-translated region functional in plants to cause the addition of polyadenylated nucleotides to the 3' end of the RNA sequence. Promoters functional in plant cells may be obtained from a variety of sources such as plants or plant DNA viruses. The selection of a promoter used in expression cassettes will determine the spatial and temporal expression pattern of the construction in the transgenic plant. Selected promoters may have constitutive activity and these include the CaMV 35S promoter, the actin promoter (McElroy et al. Plant Cell 2:163-71 (1990); McElroy et al. Mol. Gen. Genet. 231:150-160 (1991); Chibbar et al. Plant Cell Rep. 12:506-509 (1993), and the ubiquitin promoter (Binet et al. Plant Science 79:87-94 (1991), Christensen et al. Plant Mol. Biol. 12:619-632 (1989); Taylor et al. Plant Cell Rep. 12:491-495 (1993)). Alternatively, they may be inducible e.g., wound-induced (Xu et al., Plant Mol. Biol 22:573-588 (1993), Logemann et al., Plant Cell 1:151-158 (1989), Rohrmeier & Lehle, Plant Mol. Bio. 22:783-792 (1993), Firek et al. Plant Mol. Biol. 22:129-142 (1993), Warener et al. Plant J. 3:191-201 (1993)) and thus drive the expression of the mutant PAP gene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent Application WO 93/07278, for example, describes the isolation of the maize trpA gene that is preferentially expressed in pith cells. Hudspeth et al., Plant Mol. Biol. 12:579-589 (1989), have described a promoter derived from the maize gene encoding phosphoenolpyruvate carboxylase (PEPC) which directs expression in a leaf-specific manner. Alternatively, the selected promoter may drive expression of the gene under a light induced or other temporally regulated promoter. A further alternative is that the selected promoter be chemically regulated.

A variety of transcriptional cleavage and polyadenylation sites are available for use in expression cassettes. These are responsible for correct processing (formation) of the 3' end of mRNAs. Appropriate transcriptional cleavage and polyadenylation sites functional in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1:1183-1200 (1987)). In the same experimental system, the intron from the maize bronze-l gene had a similar effect in enhancing expression (Callis et al., supra.). Intron sequences have been routinely incorporated into plant transformation vectors, typically within the non-translated leader. A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic mottle Virus (MCMV), and Alfalfa Mosaic Virus (AMV) have been shown to be effective in enhancing expression (e.g. Gallie et al. Nucl. Acids Res. 15:8693-8711 (1987); Skuzeski et al. Plant Mol. Biol. 15:65-79 (1990)).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing et al., Gene 19:259-268 (1982); Bevan et al., Nature 304:184-187 (1983)), the bar gene which confers resistance to the herbicide phosphinothricin (White et al., Nucl. Acids Res. 18:1062 (1990); Spencer et al., Theor. Appl. Genet. 79:625-631 (1990)), the hph gene which confers resistance to the antibiotic hygromycin, and the dhfr gene, which confers resistance to methotrexate. Vectors suitable for *Agrobacterium* transformation typically carry at least one T-DNA border sequence. These include vectors such as pBIN19 and pCIB200 (EP 0 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g., PEG and electroporation) and microinjection. The choice of vector depends largely on the preferred selection for the species being transformed. For example, pCIB3064 is a pUC-derived vector suitable for the direct gene transfer technique in combination with selection by the herbicide basta (or phosphinothricin). It is described in WO 93/07278 and Koziel et al. (Biotechnology 11:194-200 (1993)).

An expression cassette containing the mutant PAP gene DNA containing the various elements described above may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3:2717-2722 (1984), Potrykis et al., Mol. Gen. Genet. 199:169-177 (1985), Reich et al., Biotechnology 4:1001-1004 (1986), and Klein et al., Nature 327: 70-73 (1987). In each case the transformed cells are regenerated to whole plants using standard techniques.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident plasmid or chromosomally (e.g. strain CIB542 for pCIB200 (Uknes et al. Plant Cell 5:159-169 (1993)). The transfer of the recombinant binary vector, to *Agrobacterium* is accomplished by a triparental mating procedure using *E. coli* carrying the recombinant binary vector, a helper *E. coli* strain which carries a plasmid such as pRK2013 which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16:9877 (1988)).

Transformation of the target plant species by recombinant *Agrobacterium* usually involves co-cultivation of the *Agrobacterium* with explants from the plant and follows protocols known in the art. Transformed tissue is regenerated on selectable medium carrying an antibiotic or herbicide resistance marker present between the binary plasmid T-DNA borders. Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093-1096 (1986)). Published Patent Applications EP 0 292 435, EP 0 392 225 and WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603-618 (1990), and Fromm et al., Biotechnology 11:194-200 (1993), describe techniques for the transformation of elite inbred lines of maize by particle bombardment.

Transformation of rice can also be undertaken by direct gene transfer techniques utilizing protoplasts or particle bombardment Protoplast-mediated transformation has been described for Japonica-types and Indica-types (Zhange et al., Plant Cell Rep. 7:739-384 (1988); Shimamoto et al. Nature 338:274-277 (1989); Datta et al. Biotechnology 8:736-740 (1990)). Both types are also routinely transformable using particle bombardment (Christou et al. Biotechnology 9:957-962 (1991)).

Patent Application EP 0 332 581 described techniques for the generation, transformation and regeneration of Pooideae protoplasts. Furthermore wheat transformation has been described by Vasil et al., Biotechnology 10:667-674 (1992), using particle bombardment into cells of type C long-term regenerable callus, and also by Vasil et al., Biotechnology 11:1553-1558 (1993), and Weeks et al., Plant Physiol. 102: 1077-1084 (1993), using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); and U.S. Pat. Nos. 4,849,355 and 4,663,292.

The transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See e.g. Newell et al., Plant Cell Rep. 10:30-34 (1991) (disclosing potato transformation by stem culture).

The PAP mutants confer resistance to a broad spectrum of fungal and/or viral diseases to plants. Examples of such plants are flowering plants including monocots (e.g., cereal crops)

and dicots. Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax and coffee. As an alternative to preparing transgenic plants containing an exogenous mutant PAP gene (or a PAP transgene), the PAP mutant protein may be applied directly onto the plants.

Another aspect of the present invention is directed to bioconjugates containing the PAP mutants. Fusion proteins are hybrid proteins containing a polypeptide toxin and a targeting moiety made by recombinant DNA technology. Thus, the toxic and targeting moieties are joined together via a peptide bond. See, U.S. Pat. Nos. 4,675,382 and 5,616,482 (the "'382 and the '482 patents"). Immunotoxins on the other hand are not fusion proteins; in these cases, the toxic moiety and the targeting moieties are linked via a non-peptide bond. Thus, in the case of immunotoxins, the targeting moiety does not have to be peptidic in nature. The targeting moiety will cause binding of the immunotoxin or fusion protein (collectively "bioconjugate") to a target cell such as a cancer cell, a T-cell, monocyte or macrophage. Thus, in its broadest context, the bioconjugates of the present invention may be used to target any unwanted cell to which it will bind. The targeting moiety is selected as to preferentially bind to the target cells to the substantial exclusion of non-target (e.g., non-diseased) cells because the receptor or binding partner that binds the targeting moiety is not present on or in the target cell, or is present but in significantly fewer numbers so as to reduce unwanted side effects.

The bioconjugates in the form of an immunotoxin may be prepared by a process involving preparing the recombinant PAP by (i) cloning a DNA sequence that encodes the PAP mutant into an expression vector; (ii) transforming *E. coli* cells or other host cells with the expression vector; (iii) maintaining the transformed cells under biologic conditions sufficient for expression of the PAP mutant. Once the recombinant PAP mutant has been isolated, a suitable targeting moiety is provided such as a monoclonal antibody, monoclonal antibody fragment, or a single chain variable region polypeptide in purified form. The PAP mutant is then linked to the targeting moiety by methods of conjugation well known to those of skill in the art. For example, one such method is the utilization of a heterobifunctional crosslinker, e.g. N-succinimidyl 3-(2-pyridyldithio)propionate (SPDP). Finally, the immunotoxin is purified by size exclusion and affinity chromatography and any endotoxin is removed. A method of linking B43 to a toxic moiety (e.g., a PAP mutant of the present invention) is taught in U.S. Pat. No. 4,831,117. Yet other methods of linking the targeting moiety to the PAP mutant are taught in U.S. Pat. Nos. 4,363,758; 5,167,956 and 4,340,535. In addition to SPDP, 4-succinimidyloxycarbonyl-methyl-(2-pyridyldithio)-toluene (SMPT) and N-succimidyl 6-[3-(2-pyridyldithio)propionamido]hexanoate (LC-SPDP) are commonly used as linking agents.

Also provided in the present invention is a process for preparing a fusion toxin. Typically, the process involves constructing an expression vector comprising DNA encoding a fusion protein comprising the PAP mutant and the targeting moiety. The vector is utilized in the transformation of a non-human host such as *E. coli* cells. The transformed cells are then maintained under biologic conditions sufficient for expression of the fusion toxin. Once the fusion toxin has been expressed, it can be isolated and purified by size exclusion and affinity chromatography steps, and any endotoxin can be removed.

The general methods for constructing recombinant DNA which can transform target cells are well known to those skilled in the art, and the same compositions and methods of construction may be utilized to produce the recombinant PAP useful herein. For example, J. Sambrook et al., Molecular Cloning: A Laboratory Manual, Cold Spring Harbor Laboratory Press (2d ed., 1989), provides suitable methods of construction.

The recombinant nucleic acid can be readily introduced into the target cells by transfection with an expression vector comprising cDNA encoding PAP, for example, by the modified calcium phosphate precipitation procedure of C. Chen et al., Mol. Cell. Biol., 7:2745 (1987). Transfection can also be accomplished by lipofectin, using commercially available kits, e.g., provided by BRL. Suitable non-human hosts include cells for the expression of the recombinant PAP derived from multicellular organisms, such as yeasts, insects and plants. Such hosts are capable of complex processing and glycosylation activities. In principle, any higher eukaryotic cell culture is functional, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. See, e.g., Luckow et al., Bio/Technol, 6:47 (1988); Miller et al., in Genetic Engineering, J. K. Setlow et al., eds., Vol. 8 (Plenum Publishing, 1986), pp. 277-279; and Maeda et al., Nature, 315:592 (1985). A is variety of viral strains for transfection are publicly available, e.g., the L-1 variant of *Autographa californica* NPV and the Bm-5 strain of *Bombyx mori* NPV, and such viruses may be used, preferably for transfection of *Spodoptera frugiperda* cells.

In preferred embodiments, the bioconjugates are used for the treatment of cancer. The method comprises parenterally administering to a patient who is afflicted with cancer an effective amount of a pharmaceutical composition comprising a bioconjugate of the present invention. Preferred cancers are diseases associated with the proliferation of mammalian cells expressing antigens recognized by the preferred targeting moieties of the present invention. Such cancers include, but are not limited to, B-lineage acute lymphoblastic leukemia, chronic lymphocytic leukemia, B-lineage lymphoma, blast crisis of chronic myelocytic leukemia, hairy cell leukemia, AIDS lymphoma, EBV-lymphoma, brain tumors, neuroblastoma, osteosarcoma, soft tissue sarcoma, breast cancer, prostate cancer, ovarian cancer, testicular cancer, melanoma, lung cancer, or colon cancer. Accordingly, the mammalian cell targeted by the PAP bioconjugate will be a cancer cell or a cell on the surface of a tumor blood vessel. More preferably, the cell will be one associated with leukemia, lymphoma, a brain tumor, neuroblastoma, osteosarcoma, soft tissue sarcoma, breast cancer, prostate cancer, ovarian cancer, testicular cancer, melanoma, lung cancer, or colon cancer.

Many cancer cells overproduce cytokine receptors. Thus, the targets for this type of therapy can be growth factor receptors, differentiation antigens, or other less characterized cell S surface antigens. Accordingly, effective targeting moieties include, but are not limited to, cytokines, cytokine subunits, antibodies e.g., monoclonal antibodies, and antibody fragments and subunits e.g., monoclonal antibody fragments, single chain variable region polypeptides, and cytokines. Examples of targeting moieties include, but are not limited to, a monoclonal antibody, monoclonal antibody fragment, or single chain variable region polypeptide directed against the CD2, CD3, CD4, CD5, CD7, CD13, CD14, CD19, CD22, CD24, CD33, CD40, CD45, CD72, TXU.1, NXU.1, TP-1, or TP-3 antigen. Furthermore, the targeting moiety of the present invention may be a cytokine. If the targeting moiety is a cytokine, preferred cytokines include, but are not limited to, GM-CSF, IL-2, IL-3, IL4, IL-6, IL-7, IL-8, IL-9, IL-10, IL-12, EGF, FGF, PDGF, or NGF. See also the '382 and the '482 patents.

Preferably, the targeting moiety will be a monoclonal antibody, monoclonal antibody fragment, or an antibody-derived single chain variable region polypeptide, that binds to the surface of cancer cells or tumor blood vessels. Most preferably, the targeting moiety will be a monoclonal antibody, monoclonal antibody fragment, or single chain variable region polypeptide directed against the CD2, CD3, CD4, CD5, CD7, CD13, CD19, CD22, CD24, CD33, CD40, CD45, CD72, TXU.1, NXU.1, TP-1, or TP-3 antigen.

In some embodiments, the targeting moiety is a cytokine or single chain variable region polypeptide derived from an antibody which does not bind to a receptor expressed on normal pluripotent bone marrow progenitor cells. If the targeting moiety is a cytoline, it is preferred that it be GM-CSF, IL-2, IL-3, IL-4, IL-6, IL-7, IL-8, IL-9, IL-10, IL-12, EGF, FGF, PDGF, or NGF. If the targeting moiety is a single chain variable region polypeptide, it is preferred that it be directed against the CD2, CD3, CD4, CD5, CD7, CD13, CD19, CD22, CD24, CD33, CD40, CD45, CD72, IXU.1, NXU.1, TP-1, or TP-3 antigen. More preferably, the single chain variable region polypeptide is the Fab fragment, e.g., of antibody B43. B43 is a murine IgG1, alpha.monoclonal antibody (MoAb) recognizing a 95 kDa target B lineage restricted phosphoglycoprotein, which is identified as the CD19 antigen according to the World Health Organization (WHO) established CD (cluster of differentiation) nomenclature. The chemical, immunological and biological features of B43 MoAb have been described in detail in previously published reports. Uckun et al., Blood, 71:13 (1988).

The bioconjugates of the present invention may also be used for the treatment of AIDS. In these embodiments, it is preferred that the targeting moiety be a monoclonal antibody, monoclonal antibody fragment, or antibody-derived single chain variable region polypeptide that binds to the surface of T-cells or monocytes or macrophages. Most preferably, the targeting moiety will be a monoclonal antibody, monoclonal antibody fragment, or single chain variable region polypeptide directed against the CD2, CD3, CD4, CD5, CD7, CD14 or TXU.1 antigen. In embodiments where the bioconjugate is in the form of a fusion protein, it is preferred that the targeting moiety be a cytokine that binds to the surface of T-cells or monocytes or macrophages. Most preferably, the targeting moiety will be M-CSF, GM-CSF, IL-2, IL-3, IL4, IL-6, IL-7, IL-8, IL-9, IL-10, or IL-12.

The bioconjugates of the present invention also provide the basis for an effective method to inhibit other retroviruses (HTLV-1, etc.) and viruses other than retroviruses including, but not limited to, members of the herpes virus group (HSV, CMV, EBV), influenza viruses, rhinoviruses, papovaviruses (human papilloma), adenoviruses, hepatitis virus, and the like, and diseases associated therewith. The bioconjugates may also be useful in the treatment of autoimmune diseases characterized by proliferations of unwanted cells such as T-cells or B-cells. See, U.S. Pat. No. 5,011,684.

The present bioconjugates can be formulated as pharmaceutical compositions and administered to a human or other mammal afflicted with a condition treatable by these agents, alone or in combination in a unit dosage form comprising an effective amount of one or more of these agents in combination with a pharmaceutically acceptable carrier or vehicle. It is preferred that the bioconjugates be parenterally administered, i.e., intravenously, or subcutaneously by infusion or injection. Solutions or suspensions of the bioconjugates can be prepared in water, or isotonic saline, such as PBS, optionally mixed with a nontoxic surfactant. Dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms.

Additionally, more specific delivery of the bioconjugates to the lungs may be accomplished via aerosol delivery systems. The pharmaceutical dosage form suitable for aerosol delivery can include adipot formulations such as a liposome of suitable size.

The pharmaceutical dosage form suitable for injection or infusion use can include sterile aqueous solutions or dispersions or sterile powders comprising the bioconjugates which are adapted for the extemporaneous preparation of sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the bioconjugates in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

Furthermore, suitable formulations for the bioconjugates of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy.

Such methods include the step of bringing into association the biotherapeutic agent with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The bioconjugates may also be formulated for intra-nasal or ocular administration. In this form of administration, the active ingredient may be used as a liquid spray or dispersible powder or in the form of drops. Drops, for example, eye drops, may be formulated with an aqueous or non-aqueous base also comprising one or more dispersing agents, solubilizing agents or suspending agents. Liquid sprays are conveniently delivered from pressurized packs.

For administration by inhalation, the bioconjugates are conveniently delivered from an insufflator, nebulizer or a pressurized pack or other convenient means of delivering an aerosol spray. Pressurized packs may comprise a suitable propellant such as dichlorodifluoromethane, trichlorofluromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the bioconjugates may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler of insufflator.

Additionally, the bioconjugates as well as the free recombinant PAP are well suited to formulation or controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted depot sustained release dosage forms.

The dosage of the bioconjugates in said composition can be varied widely, in accord with the size, age and condition of the patient and the target cancer. Based on animal data, it is expected that the dosage can be varied between 0.025 mg/kg/day and 1 mg/kg/day, administered over a period of about 3 to 5 days. Other details regarding how to prepare and administer the bioconjugates may be found in U.S. Pat. No. 6,146,628.

The present invention will now be further described in the course of the following examples. They are merely illustrative of work underlying the invention or of various embodiments of the invention, and thus should not be construed as limiting in any way.

EXAMPLE 1

Induction of PAP expression in yeast is known to have a cytotoxic effect (1). This cytotoxicity was presumed to be a result of translation inhibition due to depurinated rRNA. This example provides evidence that PAP depurination can occur in the absence of cytotoxicity and that both events are independent. It also describes a nontoxic mutant form of PAP that retains full antiviral activity and is expressed to significantly high levels in both plants and yeast host systems. The mutants were isolated by engineering several mutations into specific regions of the PAP gene. Following the mutagenesis, the resulting clones were screened for toxicity, viability, as well as depurination activity in yeast. Several of these isolated mutants (as shown in Table 1) were found to depurinate ribosomes in the absence of toxicity. One of these isolated proteins was studied in tobacco plants to demonstrate the presence and magnitude of antiviral activity.

Plasmids

Construction of the Mutant PAPY123A

The tyrosine codon at position 123 in pMON8588 (PAP-wild type (wt) in pGEM) was mutated to an alanine codon (TAT to GCT) using the QuikChange site-directed mutagenesis kit (Stratagene). PAPY123A was cloned into the yeast vector pNT198 containing a GAL1 promoter, PGK1 polyadenylation signal, and LEU2 auxotrophic marker resulting in pNT242. PAPY123A was also cloned into the plant expression vector pMON977 resulting in pNT220.

Construction of the Mutant PAPL251*

The leucine codon at position 251 in pMON8588 was mutated to a stop codon (CTC to TAG) using site-directed mutagenesis as described above. PAPL251* (i.e., PAP (1-250)) was cloned into the yeast vector pNT198 resulting in pNT347.

Strains and Media

*Saccharomyces cerevisiae* PSY1 (MATa ade2-1 trp1-1 ura3-1 leu2-3,112 his3-11,15 can1-100) was used for all of the yeast assays. Synthetic complete medium H lacking leucine [H-leu]) with 2% galactose or raffinose was used for controlling the induction of the PAP gene from the pNT242 and pNT347 plasmid vectors.

Induction of PAP Mutants in Yeast and Growth Curve

The PAP mutants or PAPwt were expressed in yeast from the galactose-inducible GAL1 promoter. Yeast were first grown in H-leu containing 2% raffinose to an $OD_{600}$ of 0.6. The cells were briefly pelleted at 1500g, washed once with H-leu, and resuspended at an $OD_{600}$ of 0.6 in 200 ml of H-leu containing 2% galactose for up to 10 hours. 25 ml and 5 ml were sampled from this culture every 2 hours for RNA and protein isolation, respectively. $OD_{600}$ readings were taken every hour to assess growth rates and toxicity.

Immunoblot Analyses

For analysis of protein expression in yeast, PAPY123A or PAPL251* were expressed in yeast as described above. Protein was extracted using glass beads and Buffer A (25 μM Tris pH 7.5, 1 μM EGTA, 10 μM β-glycerophosphate, 0.1 μM $Na_3VO_4$, 1 μM DTT, 5% glycerol, 1 μM PMSF) and quantified using the BIO-RAD Protein Assay reagent. 7.5 μg of total protein were separated with 12.5% SDS-PAGE and transferred to nitrocellulose as described previously (2). The blots were probed with anti-PAP antibody (1:500) overnight at 4° C. The blots were later stripped for 30 minutes with 8M guanidine HCl prior to reprobe for equal loading with anti-G6PD (1:5000). For analysis of protein expression plants, PAPY123A was expressed and extracted from plants as described previously for other transgenic plants (3). Briefly, 3 to 4 leaf discs were ground in a 1.5 ml tube in the presence of Buffer A plus plant protease inhibitors (Sigma). Forty (40) μg of crude extract were loaded as above and probed with PAP antibody (1:2000).

Depurination Analyses

Total cellular RNA was extracted as previously described (4). One (1) ug of total RNA (7.5 μg in the case of PAPL251* was additionally tested) was used for primer extension analysis to assay the depurination state of the ribosomal RNA at each of the time points described above. Primer extension was carried out using AMV reverse transcriptase (Promega) following the protocol provided by the manufacturer with the changes described here. The ribosomal primer (described in 4) was end-labeled with $^{32}P$ γ-ATP utilizing T4 kinase (Gibco-BRL). Approximately $1\times10^6$ cpm (2 ng) of labeled primer was hybridized to total cellular RNA for 15 minutes at 70° C. then 1 hour at 43° C. in formamide buffer (40 mM PIPES, 1 mM EDTA, 0.4M NaCl, 80% deionized formamide). The RNA was then precipitated with 10% 1 g of tRNA and resuspended in AMV-RT buffer and extended at 43° C. for 1 hour in a volume of 10 μl. The reaction was stopped with addition of 10 .mu.l of stop solution (USB) and 5 μl was analyzed on a 6% denaturing urea-acrylamide gel. The site of ribosomal depurination was subcloned into a vector and sequenced to provide a size marker. The intensity of the depurination was quantified with a PHOSPHORIMAGER and normalized to a higher MW extension product. Measurement of depurination of ribosomes by PAP proteins, using primer extension, is described in Hudak et al., RNA 6:369-380 (2000).

Antiviral Studies of PAPY123A in Plants pNT220 was transformed into ABI *Agrobacterium* and genetically engineered into *Nicotiana tabacum* NN plants via an *Agrobacterium*-mediated transformation procedure previously described in Lodge et al., PNAS 90:7089-7093 (1993). The R1 transgenic plants were inoculated with tobacco mosaic virus (TMV) at the concentration of 2 μg/ml to test for virus resistance (Lodge et al.). Local lesion numbers caused by TMV infection of inoculated leaves were counted and compared to non-transgenic wilt-type plants. pNT220 was also genetically engineered into *N. tabacum* nn plants as described above. The R1 transgenic plants were inoculated with potato virus X (PV at the concentration of 10 μg/ml to test for virus resistance (Lodge et al.) Local lesion numbers caused by PVX infection of inoculated leaves were counted and compared to non-transgenic wild-type plants.

Results

Growth Curves

The results are graphically illustrated in FIG. 1. While the expression of PAPwt in yeast was toxic, the expression of both PAPY123A and PAPL251* were nontoxic.

Immunoblot Analysis

Yeast

Immunoblot analysis for PAPwt indicated that protein was produced at 2 hours post-induction and increased a slight bit to reach a plateau of expression by 10 hours post-induction. Results for PAPY123A showed protein expression at 2 hours to be similar to PAPwt but the abundance increased exponentially to 10 hours. PAPL251* showed abundant protein at 2 hours post-induction (greater than both PAPwt and PAPY123A), but reached a plateau soon after. The normalization of PAP protein to G6PD protein in all three cases confirmed equal protein loading.

Plants

Immunoblot analysis for PAPY123A in transgenic plant lines showed abundant protein expression as compared with PAPx and PAPv, two other mutant forms of PAP.

Depurination Activity

Figure 2A:
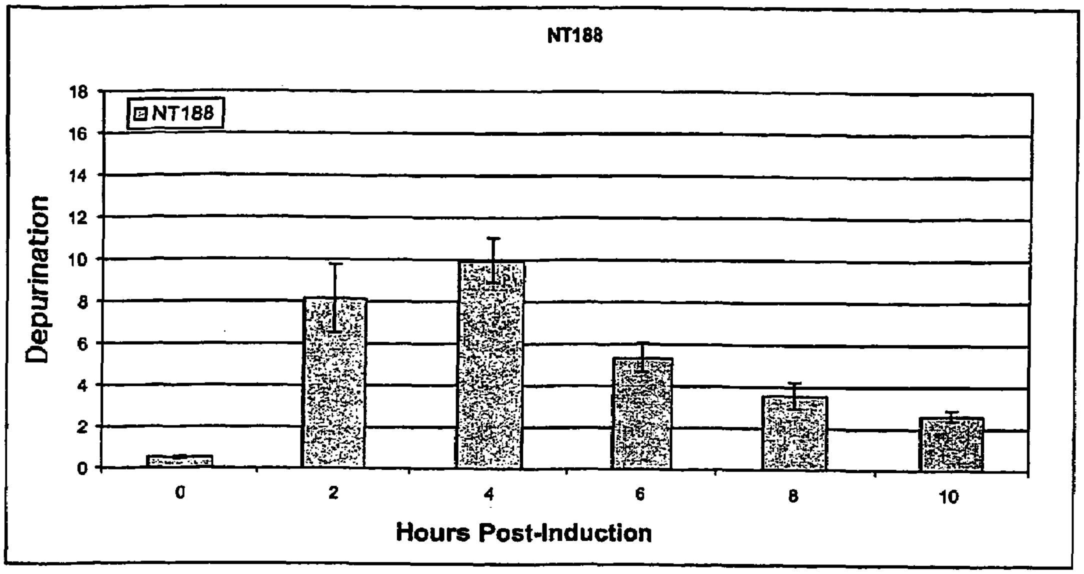
FIGS. 2A, 2B and 2C are bar graphs showing depurination activity of wild-type PAP (PAPwt) and two PAP mutants of the present invention respectively, that are expressed in yeast cells.

The results of PAPwt depurination graphically illustrated in FIG. 2A indicate that PAP can depurinate ribosomes by 2 hours post-induction and that maximal depurination occurs at 4 hours post-induction. After maximal depurination, the relative amounts of depurinated rRNA decreases.

Figure 2B:
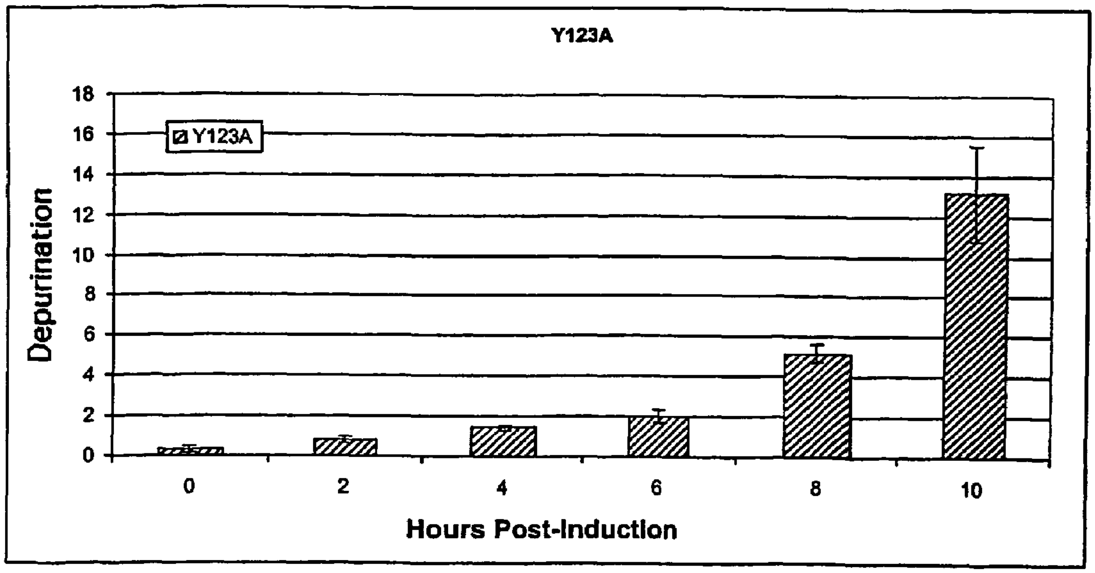

The results of PAPY123A depurination graphically illustrated in FIG. 2B indicate that the mutant protein depurinates but does so after a lag period. PAPY123A depurination of rRNA begins to surpass PAPwt depurination at 8 hours-post-induction and is quite actively depurinating ribosomes at 10 hours post-induction. This is very different from what is seen by PAPwt.

Figure 2C:
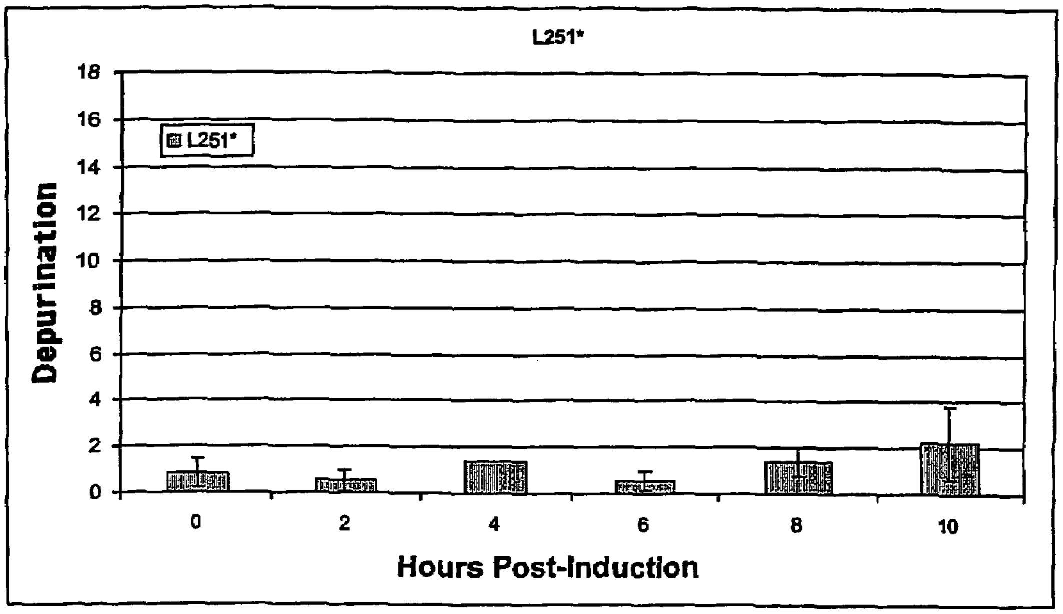

The results of PAPL251* depurination graphically illustrated in FIG. 2C indicate that the mutant protein depurinates but at a greatly reduced rate. In fact, higher starting amounts of total cellular RNA were required to appreciate the levels of depurination. PAPL251* depurination of rRNA remains below levels of PAPwt depurination at all hours-post-induction. Again, this is very different from what is seen by PAPwt. This graph is a composite of two experiments, one using 1 μg and the other using 7.5 μg of total cellular RNA as starting material.

Antiviral Studies of PAPY123A in Plants

As Table 1 demonstrates, the local lesion numbers caused by TMV infection on the inoculated leaves of the NT220-transgenic plants were significantly lower to the numbers on the non-transgenic wild-type (wt) plants.

TABLE 1

Resistance of transgenic tobacco NN plants (PAPY123A) to infection by TMV

| Line # | Local Lesion # Experiment 1 | Local Lesion # Experiment 2 |
|---|---|---|
| NT220-5-1 | 23 | 40 |
| NT220-5-2 | 12 | 12 |
| NT220-5-3 | 14 | 8 |
| NT220-5-4 | 11 | 30 |
| NT220-5-5 | 4 | 20 |
| NT220-5-6 | 12 | 31 |
| NT220-5-7 | 30 | 5 |
| NT220-5-8 | 5 | 20 |
| NT220-5-9 | 16 | 45 |
| NT220-5-10 | 9 | 24 |
| | Avg. = 13.6 ± 7.9 | Avg. = 23.5 ± 15.2 |
| wt1 | 130 | 120 |
| wt2 | 120 | 150 |
| wt3 | 150 | 150 |
| wt4 | 140 | 160 |
| wt5 | 150 | 130 |
| wt6 | 120 | 150 |
| wt7 | 120 | 160 |
| wt8 | 150 | 140 |
| wt9 | 120 | 120 |
| wt10 | 150 | 130 |
| | Avg. = 135 ± 14.3 | Avg. = 141 ± 15.2 |

The data in Table 2 demonstrate that the local lesion numbers caused by PVX infection on the inoculated leaves of the NT220-transgenic plants were significantly lower than the numbers on the non-transgenic wild-type (wt) plants.

TABLE 2

| Resistance of transgenic tobacco nn plants (PAPY123A) to infection by PVX | |
|---|---|
| Line # | Local Lesion # |
| NT220-2-1 | 40 |
| NT220-2-2 | 35 |
| NT220-2-3 | 45 |
| NT220-2-4 | 40 |
| NT220-2-5 | 47 |
| NT220-2-6 | 60 |
| NT220-2-7 | 38 |
| NT220-2-8 | 60 |
| | Avg. = 45.6 ± 9.6 |
| wt1 | 80 |
| wt2 | 90 |
| wt3 | 75 |
| wt4 | 60 |
| wt5 | 90 |
| wt6 | 95 |
| wt7 | 80 |
| wt8 | 70 |
| | Avg. = 80 ± 11.6 |

Discussion

This is believed to be the first demonstration of a mutant form of PAP which allows cells expressing the mutant protein to continue growing normally in the face of depurination.

The expression profiles indicate that an abundant amount of protein was produced in PAPY123A and that this protein was responsible for depurination. The observation that PAPY123A depurinates ribosomes only when the mutant PAP is expressed at very high levels might indicate that this is a concentration effect. That is, once the concentration of PAP reaches a certain level, a threshold for depurination is breached and the effects on rRNA can be seen. In the case of PAPL251*, protein expression is subdued as is depurination yet protein expression continues above PAPwt levels while depurination is steady at levels below PAPwt.

1. Hur et al., Proc. Natl. Acad. Sci. U.S.A. 92:8448 (1995)
2. Hudak et al., J. Biol. Chem 274:3859 (1999)
3. Lodge et al., Proc. Natl. Acad. Sci. U.S.A. 90:7089 (1993)
4. Cui et al., EMBO J. 15:5726 (1996)

EXAMPLE 2

Figure 3A:
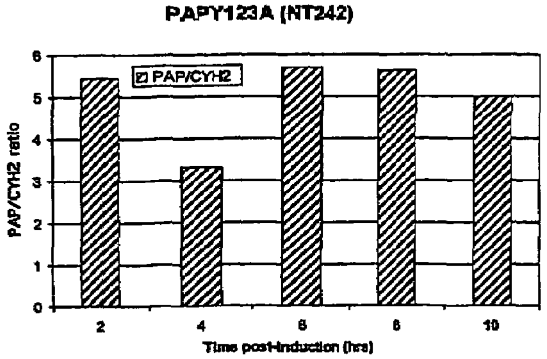
FIGS. 3A and 3B are bar graphs showing effect of expression of a PAP mutant of the present invention and PAPwt respectively, on production of their mRNA, as a function of time.
Figure 3B:
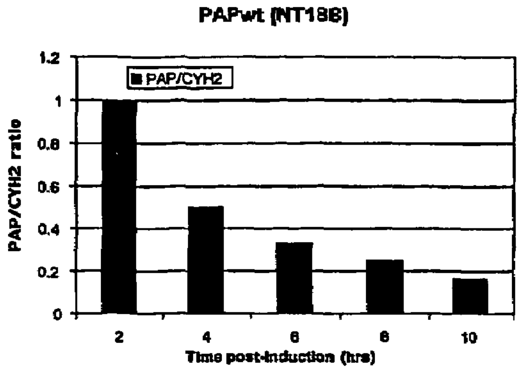

PAPY123A does not autoregulate the accumulation of its own mRNA To measure the effect of PAPwt and PAPY123A on accumulation of its mRNA, Yeast cells, containing NT242 were harvested at various times after induction by galactose, and the level of PAP mRNA was measured by RNase protection assay. A 252 nt [$^{32}$P]-labeled minus-strand RNA corresponding to the 3' end of PAP mRNA was transcribed and hybridized in the presence of excess probe with total RNA extracted from cells harboring PAPwt and PAPY123A plasmids. A 281 nt [$^{32}$P]-labeled minus-strand CYH2 RNA, which encodes the constitutively expressed ribosomal protein L29, served as the internal loading control (Fried et al., Nucleic Acids Res. 10:3133-3148 (1982)). Samples were electrophoretically separated and the intensities of the protected bands were quantified using a PHOSPHORIMAGER. The ratios for signals from the PAPwt or PAPY123A mRNAs to the CYH2 mRNA were used as relative measures of the steady-state abundance of the PAPwt and PAPY123A mRNAs. As the expression of PAPwt was induced, the level of PAPwt mRNA decreased dramatically relative to the CYH2 mRNA. See FIG. 3A. At ten hours post-induction, PAPwt mRNA levels had decreased to about 10% of the levels observed at two hours post-induction. The mutant PAPY123A did not manifest such a decrease in the level of its mRNA and quite contrary to PAPwt, the mRNA levels between two and ten hours were quite similar. See FIG. 3B. Accordingly, this PAP mutant of the present invention can be produced in hosts at relatively high levels compared to wild-type PAP.

EXAMPLE 3

Figure 4:
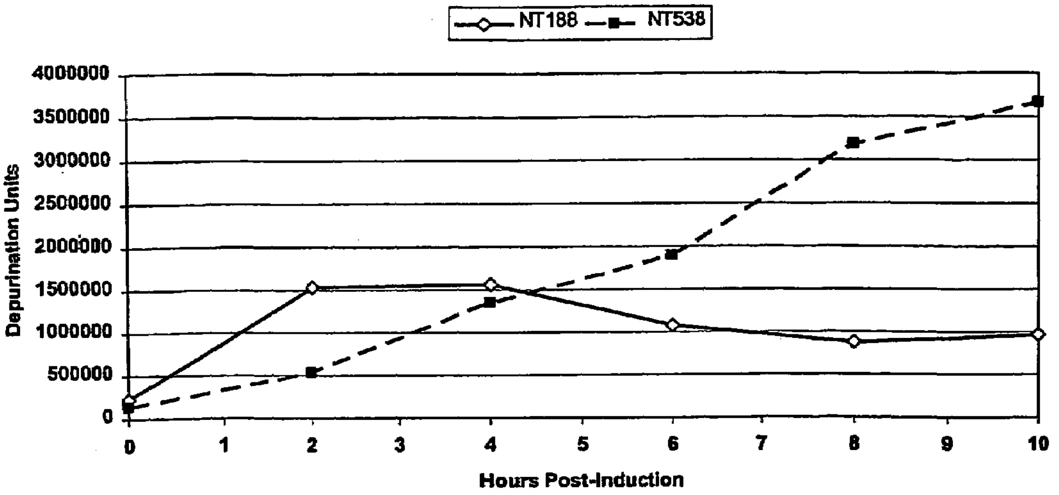
FIG. 4 is a graph showing depurination activity of a PAP mutant of the present invention PAPL71R (NT538) and PAPwt (NT188).
Figure 5A:
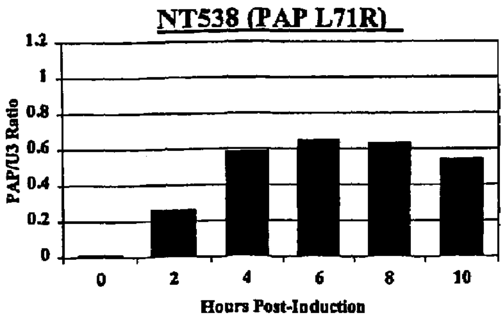
FIGS. 5A and B are bar graphs showing the effect of expression of a PAP mutant of the present invention, PAP L71R (NT538) and PAPwt (NT188) respectively, on the stability of their mRNA FIG. 6A (1 and 2) are photographs of plates showing serial dilution of yeast cells growing on media containing glucose, wherein the yeast express PAPwt (1) and a PAP mutant of the present invention PAP L71R (NT538) (2).
Figure 5B:
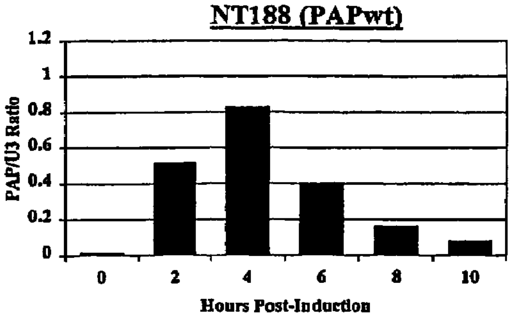

To examine the relationship between ribosome depurination and mRNA destabilization in cells expressing PAP, a highly sensitive primer extension analysis was used to examine the extent of ribosome depurination and mRNA turnover at different times after induction of PAP expression. PAP mRNA levels were quantified by RNAse protection analysis using the U3 RNA as the internal control. Quantification of the level of depurination in the RNA samples from wild type PAP (NT188) and L71R PAP (NT538) indicated that depurination was detected two hours after PAP induction and maximal depurination of rRNA in the cell occurred by between 2-4 hours after induction (FIG. 4). RNase protection analysis of mRNA levels indicated that wild type PAP mRNA levels increased up to four hours on galactose (FIG. 5B). PAP mRNA was destabilized after 4 hours even when transcription was not repressed, indicating that the rate of RNA degradation exceeded the rate of RNA synthesis (FIG. 5B). Ribosome depurination decreased slightly after four hours, while PAP mRNA levels decreased dramatically. These results indicate that rRNA can be depurinated in conditions when PAP mRNA is not degraded. This is consistent with previous results, which indicate that low levels of PAP present after transcription and translation shut-off can depurinate the rRNA in trans. The depurination of rRNA could precede the destabilization of mRNA or the two events could be independent.

To determine if rRNA depurination could be separated from mRNA destabilization, a nontoxic PAP mutant, NT538 (L71R) which depurinates ribosomes was tested. By 4 hours post induction, similar levels of depurination are observed in NT188 and NT538 (FIG. 4) cells. However, after 4 hours, the depurination in cells containing NT538 increases to much higher levels than in NT188 (FIG. 4). RNase protection analysis of PAP mRNA levels in NT538 cells indicated that PAP mRNA is not destabilized in NT538 cells after 4 hours of induction even though the ribosomes are depurinated at higher levels than in NT188 cells. (FIG. 5A) These results indicate that the activity of PAP on rRNA can be dissociated from its effects on mRNA stability.

Figure 6A:
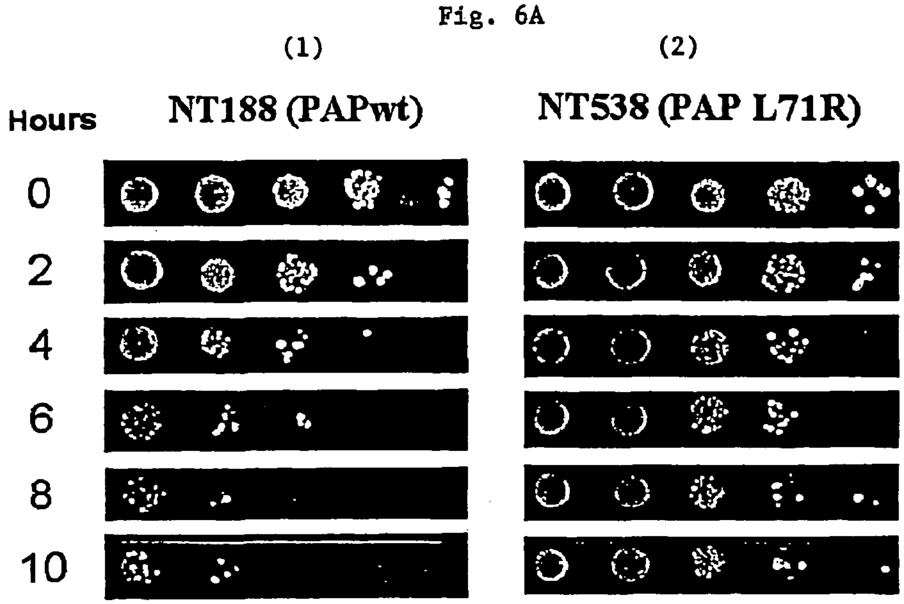
FIG. 6B is a bar graph showing the quantification of the viability assay and a comparison of yeast colony forming units at indicated times after induction of expression of a PAP mutant of the present invention PAPL71R (NT538) and PAP wt.
FIG. 6C is a graph showing growth of yeast that produce a PAP mutant of the present invention, yeast that produce the nontoxic PAP mutant (E176V) and yeast that produce wild type PAP.
Figure 6B:
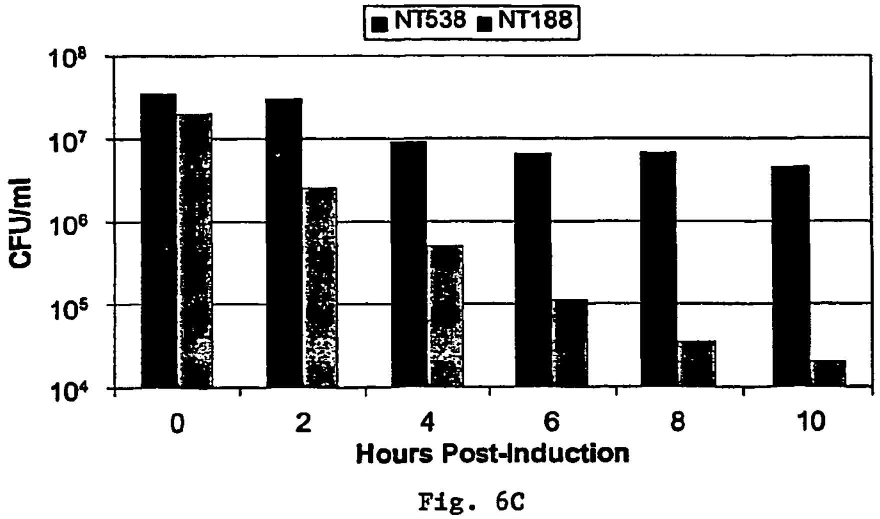
Figure 6C:
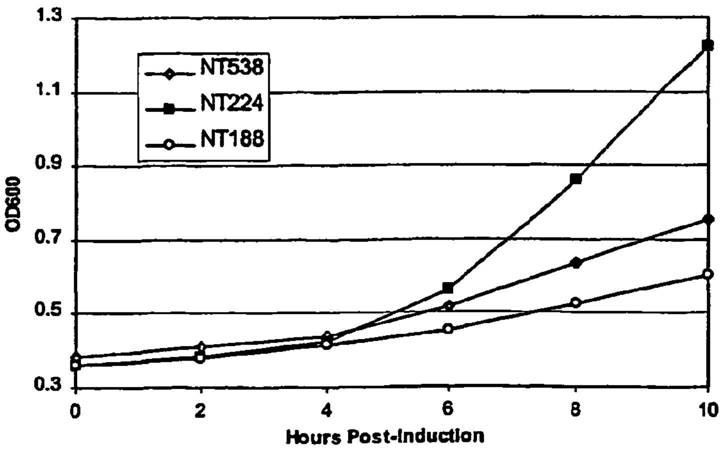

To examine the impact of rRNA depurination and mRNA destabilization on cell viability, cells containing NT188 or NT538 plasmid were grown on liquid H-Leu media containing galactose and different dilutions were plated on H-Leu plates containing glucose. The colony forming units were counted based on the dilution analysis. As shown in FIGS. 6A and 6B, the results of the viability analysis indicated that cell viability decreases logarithmically in PAP expressing cells up to 10 hours post induction. In contrast, there is very little decrease in cell viability L71R PAP expressing cells. At 10 hours post-induction, NT538 (PAP-L71R) was only reduced in viability by 0.9 log or about 9-fold whereas NT188 (PAPwt) was reduced in viability by 3.3 log or about 2000-fold as compared with NT224 (PAPx). These results suggest that the decrease observed in cell viability does not correlate with rRNA depurination or inhibition of translation, but does correlate with mRNA destabilization. Therefore, viability of cells expressing PAP L71R is not significantly reduced because this mutant does not affect mRNA stability, even though it depurinates mRNA. These results indicated that inhibition of growth does not necessarily lead to inhibition of cell viability because cells containing NT538 are inhibited in growth, but not viability. As shown in FIG. 6C, growth on liquid media correlates with the ability to depurinate rRNA and inhibit translation, but not viability.

EXAMPLE 4

Isolation and Characterization of Pokeweed Antiviral Protein Mutations in *Saccharomyces cerevisiae*: Identification of Residues Important for Cytotoxicity and Depurination of rRNA To identify residues critical for cytotoxicity of PAP, systematic deletions were made from the 5' and the 3' ends of the PAP cDNA. Cytotoxicity and the ability of the mutant proteins to depurinate yeast ribosomes in vivo were examined.

Results of these assays demonstrated that truncating the first 16 amino acids of PAP by introducing a Met in place of Tyr at position 16 (Y16M) eliminated the cytotoxicity of PAP and its ability to depurinate ribosomes. Point mutations at Y16 (Y16A or Y16F) did not inhibit cytotoxicity or depurination of ribosomes, indicating that Y16 alone is not responsible for cytotoxicity. Deletion of the first 13 amino acids of PAP, by introducing a Met in place of Ser14 did not affect the cytotoxicity of PAP or its depurination ability. However, combination of the S14M mutation with a mutation in Y16 (Y16A) resulted in a nontoxic protein, which depurinated ribosomes, indicating that Y16 and S14 are critical for cytotoxicity, but not depurination of ribosomes. These results indicate that cytotoxicity of PAP is not entirely due to depurination of ribosomes.

Deletion analysis of the C-terminal domain of PAP indicated that a nonsense codon introduced at L252 eliminated the cytotoxicity of PAP, but not its depurination activity. Mutation of Leu 252 to Lys (L252K) did not affect cytotoxicity or depurination activity, suggesting that Leu 252 by itself is not critical for cytotoxicity. Depurination activity of PAP was abolished when a stop codon was introduced at R241, indicating that residues critical for ribosome depurination are downstream of R241.

These results demonstrate that sequences responsible for cytotoxicity of PAP and its depurination activity can be separated at the C-terminus of PAP, providing evidence that cytotoxicity of PAP is not necessarily a direct result of depurination.

Materials and Methods

Mutations of PAP cDNA were achieved by using the Stratagene QUICKCHANGE site-directed mutagenesis kit. Mutations were introduced into a set of oligomeric primers that were used for PCR-amplifications of the template plasmid pMON8588 with wild type PAP in pGEM (Promega) background by Pfu DNA polymerase. After PCR-amplifications, the template plasmid pMON8588 was removed by DpnI digestion. The mutated plasmids were transformed into *Escherichia coli* DH5. Mutant plasmids were confirmed by sequencing using the 17 SEQUENASE Version 2.0 sequencing kit (USB). cDNAs encoding PAP N-terminal mutants were subcloned as Bam HI-Hind III m fragments into the yeast expression vector YEp351 under the control of a galactose-inducible GAL1 promoter.

Yeast Transformation: Yeast cells (*Saccharomyces cerevisiae* strain W303 (MAT α, ade2-1 trp1-1 ura3-1 leu2-3, 112 his3-11, 15 can1-1000) were transformed according to Ausubel et al., (1994). The transformed yeast suspension was divided in half and half was plated onto H-leu supplemented with 2% dextrose and the other half onto H-leu with 2% galactose.

Transformed yeast was allowed to grow for 72 hours at 30° C. Toxicity of the PAP mutants was verified by re-plating selected colonies onto both 2% raffinose and 2% galactose.

Growth curves: Yeast transformed with either wild type or mutant forms of PAP were grown in synthetic H-leu medium supplemented with 2% raffinose at 30° C. with shaking at 240 r.p.m. in a total volume of 100 ml until an A600=0.6. Yeast cells were pelleted by centrifugation at 2,000×g for 5 min, washed with H-leu medium and resuspended in H-leu medium containing 2% galactose to induce the expression of PAP or PAP mutants. At zero time (immediately following induction) and at each hour following induction, 1 ml aliquots were removed and A600 measured. Doubling times were calculated from the growth curves and compared to the doubling time of PAPwt.

Yeast Protein Expression Analysis: Yeast containing cDNAs of PAP or PAP mutants were grown as described for growth curves, in a 10 ml volume and induced with 2% galactose for 6 h. Cells were pelleted by centrifugation at 2,000×G for 5 min. Pellets were resuspended in an equal volume of cold (4° C.) Buffer×(25 mM Tris-HCl pH 7.5, 100 mM sodium vanadate, 10 mM β-glycophosphatase, 1 mM EGTA, 1 mM DTT, 1 mM PMSF, 5% glycerol) and 0.3 g of 0.5 mm diameter glass beads. Cells were vortexed for 2 mm and centrifuged at 16,000×g for 5 min. Supernatant total protein was quantified by Bradford using BSA as a standard. Total protein (15 μg) was separated through 12% SDS-PAGE, transferred to nitrocellulose, and blocked by incubation with PBST (phosphate buffered saline with 0.1% TWEEN 20) in 5% nonfat milk for 2 h. Proteins were probed by overnight incubation with an affinity purified polyclonal antibody to PAP (1:5000) in PBST-5% milk and secondary goat anti-rabbit IgG conjugated to horseradish peroxidase (1:5000) in PBST-5% milk for 1.5 h. Mutant PAP proteins were visualized by chemiluminescence using a RENAISSANCE kit (NEN, DuPont). To confirm equal loading of total protein, blots were stripped with 8 M guanidine hydrochloride and reprobed with a polyclonal G6PD (1:5000; Chemicon, Temecula, Calif.) and horseradish peroxidase conjugated secondary donkey anti-goat IgG (1:5000).

rRNA Depurination Assay. Yeast cells (100 ml) grown as described for growth curves, were harvested following a 6 h induction of PAP and PAP mutants and used to isolate ribosomes as previously described (Hudak et al., 1999). To determine if PAP mutants depurinated the S/R loop when expressed in vivo, primer extension analysis was preformed essentially as described in Hudak et al., 2001. Purified ribosomal RNAs (1 μg) were incubated with a 5' [32P] end-labeled oligonucleotide primer (5'-GGCGTTCAGCCAT-AATCC-3') (SEQ ID NO:3) complementary to the 3'-end of yeast 25S rRNA. Primer extension was performed as described (Ioranov et al., 1997) with minor modifications. Namely, the total reaction volume was 15 μl, to which 5 μl of formamide buffer was added to stop the extension without the precipitation of RNA and resulting cDNA. An aliquot of this reaction (4 μl) was separated on a 6% polyacrylamide/7M urea gel and visualized by autoradiography. To determine the position of rRNA depurination, a sequencing ladder of DNA corresponding to the yeast 25S rRNA was separated on the same gel (Hudak et al., 2001)

Results and Discussion

The results are summarized in Table 3, which is appended to this example.

Mutations within the N-Terminal Domain of PAP

To identify residues that are important for cytotoxicity within the N-terminal domain of PAP, site-directed mutagenesis was used to make systematic deletions from the N-terminus and to introduce point mutations at critical residues. N-terminal deletions were made by introducing a Met codon at conserved residues and deleting the residues upstream of Met by introducing a BglII site. Protein from all mutants was expressed following 6 h induction in yeast, though expression patterns varied. Wild type PAP expressed in yeast was present in two forms, the mature protein at 29 kDa (parallel to standard lane in immunoblots) and a higher molecular weight form, presumably the precursor form of PAP seen previously in yeast lysates (Hur et al., 1995; Hudak et al., 1999). The molecular weight of C-terminal deletion mutants such as NT1246 (W237*) and NT509 (L240*) were approximately 26.5 kDa, indicating the expected lower size of these proteins missing either 26 or 23 amino acids, respectively.

Systematic deletions were made from the N-terminus of mature wild type PAP, from the $14^{th}$ to the $39^{th}$ amino acid. As shown in Table 3, deletion of the N-terminal signal peptide and 14 amino acids from the N-terminus of mature PAP (NT418, S14M) did not affect the cytotoxicity of PAP. The doubling time of yeast expressing this mutant was 7.8 h compared with 10.4 h for wild type PAP (NT188), which contains both the N-terminal signal sequence and the C-terminal extension. The level of depurination of S14M PAP was 70% of wild type PAP. Similarly, substitution of Lys with Met (NT413, K15M) resulted in a cytotoxic protein that inhibited yeast growth and depurinated ribosomes to 79% of wild type levels. These results indicated that deletion of the N-terminal signal sequence and the first 15 amino acids from the N-terminus of mature PAP does not affect its cytotoxicity or ability to depurinate ribosomes.

In contrast, changing Tyr16 to Met generated a deletion mutant that was unable to depurinate ribosomes and was also noncytotoxic when expressed in vivo, indicating that Y16 is required for cytotoxicity. Further deletions from the N-terminus, which included T18M and deletion of the N-terminus to Met 39, resulted in nontoxic proteins that did not depurinate ribosomes. These results indicated that either Y16 alone or Y16 and another amino acid upstream are required for cytotoxicity of PAP and its ability to depurinate ribosomes. Point mutations of Y16 to either Ala (NT321) or Phe (NT324) created a protein that regained both cytotoxicity and depurination ability, indicating that the tyrosine alone is not entirely responsible for these characteristics, but that amino acids upstream of this tyrosine likely contribute.

Further evidence for this was obtained when Y16A mutation was combined with a mutation of Ser14 to Met (NT472) (Table 3) The resulting double mutant (S14M,Y16A) protein lost its cytotoxicity, indicating that either Ser14 or another amino acid within the first 14 amino acids of PAP, in combination with Tyr16, contributes to the cytotoxicity of PAP. The doubling time of cells expressing NT472 was 6.8 h, similar to the growth rate of the nontoxic PAP mutant NT224 (6.4 h). However, ribosomes were depurinated in yeast expressing the double mutant (NT472), providing evidence that nbosome depurination alone does not lead to cytotoxicity. Changing the Ser to other amino acids did not result in the same inhibition. For example, exchange of the Ser for Thr (NT450) did not affect cytotoxicity or depurination activity, as may be expected because the hydroxyl group and relative size of the amino acid were maintained. The growth rate, as measured by doubling time, of NT450 was similar to cells expressing wild type PAP, 10.1 h and 10.4 h respectively, and its level of depurination was similar to wild type PAP, at 99%. Substitution of Ser for the hydrophobic amino acid Ile (NT473) or the aromatic ring amino acid Phe (NT469) resulted in toxic proteins that depurinated to levels comparable to wild type PAP.

Taken together, these results indicate that S14 alone is not responsible for cytotoxicity and S14 together with Y16 may contribute to the cytotoxicity of PAP. The double mutant form of PAP depurinated ribosomes to 79% of the level of wild type PAP, a level between that observed for the single mutations Y16A (97%) and S14M (70%). In addition, the S14MY16A PAP was nontoxic to cells i.e., doubling times were similar to yeast cells expressing PAPx, 6.8 h compared with 6.4 h, respectively. However, the cytotoxic mutant K15M depurinated ribosomes also to 79% and doubling times of yeast expressing this mutant were 8.5 h. These results indicate that nbosome depurination alone is not entirely responsible for the cytotoxicity of PAP.

Mutations within the C-terminal Domain of PAP

Sequential deletion mutants from the 3'-terminus of PAP indicate that changing the last amino acid of mature PAP to a stop codon and deleting the C-terminal extension of PAP does not affect its cytotoxicity or depurination ability. The T262* PAP is cytotoxic and depurinates ribosomes to 96% of wild type levels. The Y254* PAP is also cytotoxic and depurinates ribosomes to the same extent as wild type PAP (100%). The N253* PAP is cytotoxic, but depurinates to 64% of wild type levels. Cytotoxicity is lost when L252 is deleted (NT420). The L252* PAP is capable of depurinating ribosomes, albeit at lower levels than wild type PAP (39%). Similarly, L251* PAP is not cytotoxic and depurinates ribosomes to only 35% of the wild type levels. The lack of toxicity of both L252* and L251* PAP may be due to their lower levels of depurination relative to wild type PAP (39% and 35% respectively), suggesting that a threshold level exists at which yeast cells will tolerate some degree of nbosome depurination without reduction in overall growth rates. The relative amount of depurination measured for N253* PAP was 64%, an intermediate value between L252* measured at 39% and the toxic mutant Y254* measured at 100%. Substitution of L252 for Lys (NT457) did not alter the growth rate of cells or depurination ability of PAP, indicating that Leu252 alone is not responsible for cytotoxicity. Rather, the results indicate that L252 and residues downstream are important determinants of cytotoxicity. This observation is supported by the sequential increase in both toxicity and depurination observed between L252* and Y254*.

The C-terminal deletion analysis indicates that cytotoxicity of PAP is lost before its ability to depurinate ribosomes. Depurination ceased when a stop codon was introduced at R241. These results indicate that R241 and residues downstream are critical for ribosome depurination. Increased length of deletion from the C-terminal end resulted in a gradual decrease in both cytotoxicity and the depurination ability of PAP. These results provide further evidence that C-terminal amino acids are critical for both toxicity and nbosome depurination. It has been proposed that a cleft at the interface between the central and the C-terminal domains of PAP forms the putative substrate-binding site (Ago et al, 1994). The positively charged domain in the C-terminal region has been proposed to provide interaction with the substrate RNA (Ago et al, 1994). Therefore, the C-terminal region of PAP may be required for proper folding of the active site to interact with the substrate RNA. An alternative possibility is that the C-terminal domain may be involved in membrane interactions prior to translocation of PAP into the cytosol from the ER. It has been shown that efficient internalization of transmembrane receptor proteins requires a signal sequence in the cytoplasmic tail of the protein. At least two different types of internalization sequences based on either tyrosine or di-leucine motifs have been identified in a variety of receptor molecules. Leucine-leucine or leucine-isoleucine sequence motifs important for internalization and/or lysosomal targeting were found in the intercellular domains of various receptors. Thus, sequences downstream of R241, which include the dileucine motif in PAP, may be involved in membrane interactions prior to translocation of PAP into the cytosol. A point mutation in a proline residue in the same region of ricin, P250A, resulted in a marked reduction in cytotoxicity.

Mutations within the Central Domain of PAP.

It has been proposed that amino acids Y72 and Y123 sandwich the adenine ring of nbosomal RNA in an energetically favorable stacking conformation. Subsequently, the side chain of R179 can protonate the N-3 atom of the adenine base, while E176 stabilizes a positive oxocarbonium transition state. E176 and R179 are highly conserved amino acids within the active site of RIPs and both participate directly in the depurination of rRNA. As shown in Table 3, substitution of Y72 for Ala (NT241) resulted in a nontoxic protein that depurinated ribosomes to much lower levels than wild type PAP. The relative degree of depurination by Y72A PAP was 4% of wild type PAP, which confirms earlier reports that this amino acid is important for depurination of the rRNA. Replacement of Y123 with Ala (NT242) again produced a nontoxic form of PAP, which exhibited relatively low levels of nbosome depurination (21% of wild type levels), at 6h post-induction. However, substitution of Y123 with ne (NT485) resulted in a nontoxic mutant with growth rates of cells comparable to the active site mutant, NT224 (6.9 h and 6.4 h respectively), but with substantially higher levels of depurination. Ribosomes from cells expressing Y123I PAP were depurinated 81% relative to wild type PAP, without growth inhibition, providing further evidence that cytotoxicity of PAP may not be entirely due to ribosome depurination. Replacing Y123 with Phe (NT483) generated a toxic protein with doubling times of cells increased to 11.4 h. Y123F PAP depurinated ribosomes to 98% of control levels. Given that Y123I PAP was not toxic despite 81% nbosome depurination relative to wild type PAP, whereas Y123F PAP was toxic and also depurinated ribosomes, suggests that maintenance of the benzyl ring structure is important for toxicity of the conserved Y123 but not its rRNA depurination activity.

Analysis of central domain mutants indicates that there is not a good correlation between the extent of depurination and cytotoxicity, suggesting that factors other than the absolute level of depurination may be responsible for the cytotoxicity of PAP. Since both Y72 and Y123 are thought to be involved in substrate binding, the lower level of depurination observed with Y72A PAP could be due to lower levels of binding to substrate RNA. Y72 is within the RNP2 binding domain of PAP, which appears to be critical for binding to rRNA. A previously characterized mutant in this domain G75D PAP did not bind ribosomes efficiently. Other mutations constructed in the RNP2 domain (L71-Y76) indicated that all amino acids within this domain (L71, L72, V73, M74, G75 and Y76) are critical for cytotoxicity of PAP (Table 3). In contrast, alanine substitutions at N69 (NT502), N70 (NT501) and D92 (1T503) did not affect the cytotoxicity or the depurination ability of PAP. Previous studies showed that alanine substitutions at N69, N70, F90 and D92 substantially reduced the depurinating and ribosome inhibitory activity of PAP in vitro (Rajamohan et al., 2000). This could be due to potential differences in the localization of these proteins in vivo, all proteins in this study were expressed and characterized iii vivo. Alternatively, the assays used in the previous studies were not sensitive enough to detect low levels of depurination in vitro.

These results suggest that amino acids within the RNP2 domain (L71-Y76) of PAP are likely involved in substrate recognition. Unlike the previously published results (Rajamohan et al., 2000), the Y123A PAP mutant was still able to depurinate ribosomes. A sensitive assay, primer extension analysis, clearly indicated that Y123A PAP depurinated ribosomes to 21% of wild type PAP. Substitution of an isoleucine residue in place of tyrosine 123 increased depurination to 81% of the control levels, without affecting cytotoxicity. These results indicate that Y123 does not play a major role in substrate binding as previously thought, but does play a major role in cytotoxicity.

TABLE 3

Effect of mutations on the cytotoxicity of PAP and its ability to depurinate ribosomes.
N.D.: not determined;*:stop codon)

| | MUTATION | CYTOTOXICITY | DEPURINATION (% of control) | DOUBLING TIME |
|---|---|---|---|---|
| | | N-terminal domain Mutants | | |
| NT188 | Wild Type | Yes | Yes (100) | 10.4 |
| NT418 | S14M | Yes | Yes (70.25) | 7.85 |
| NT413 | K15M | Yes | Yes (79.44) | 8.55 |
| NT542 | Y16M | No | No (5.95) | 7.1 |
| NT549 | T18M | No | No (6.67) | 7.3 |
| NT441 | 39M | No | No (2.05) | 7.5 |
| NT525 | S14A | Yes | Yes (106.49) | 10.2 |
| NT426 | S14E | Yes | Yes (96.65) | 10.15 |
| NT449 | S14K | Yes | Yes (101.01) | 10.5 |
| NT450 | S14T | Yes | Yes (98.94) | 10.1 |
| NT469 | S14F | Yes | Yes (94.33) | 11 |
| NT473 | S14I | Yes | Yes (100.10) | 9.95 |
| NT472 | S14MY16A | No | Yes (78.62) | 6.85 |
| NT360 | K15A | Yes | Yes (83.46) | 10.2 |
| NT558 | Y16A | Yes | Yes (97.11) | 9.5 |
| NT548 | Y16F | Yes | Yes (103.86) | 11.0 |
| NT569 | S14AY16A | Yes | Yes (96.95) | 9.9 |

TABLE 3-continued

Effect of mutations on the cytotoxicity of PAP and its ability to depurinate ribosomes. N.D.: not determined;*:stop codon)

| | MUTATION | CYTOTOXICITY | DEPURINATION (% of control) | DOUBLING TIME |
|---|---|---|---|---|
| | | Central domain Mutants | | |
| NT502 | N69A | Yes | Yes (102.53) | 10.5 |
| NT501 | N70A | Yes | Yes (95.62) | 7.3 |
| NT538 | L71R | No | Yes (105.41) | 8-9 |
| NT241 | Y72A | No | No (4.05) | 6.5 |
| NT532 | V73E | No | Yes (89.59) | 7.5 |
| NT533 | M74R | No | Yes (102.6) | 8.5 |
| NT255 | G75D | No | No (0) | |
| NT534 | Y76A | No | Yes (98.51) | 6.1 |
| NT503 | D92A | Yes | Yes (101.27) | 10 |
| NT242 | Y123A | No | Yes (21.03) | 7.1 |
| NT483 | Y123F | Yes | Yes (97.84) | 11.4 |
| NT485 | Y123I | No | Yes (80.75) | 6.9 |
| NT224 | E176V | No | No (0) | 6.4 |
| | | C-terminal domain Mutants | | |
| NT246 | W237* | No | No (0) | |
| NT509 | L240* | No | No (0) | 8.2 |
| NT552 | R241* | No | No (0) | 6.2 |
| NT510 | V242* | No | Yes (5.42) | 8.25 |
| NT333 | E244* | No | Yes (3.32) | 6.45 |
| NT486 | A250* | No | Yes (42.95) | 6.8 |
| NT347 | L251* | No | Yes (34.52) | 6 |
| NT420 | L252* | No | Yes (38.92) | 6 |
| NT456 | N253* | Yes | Yes (64.15) | 6.1 |
| NT443 | Y254* | Yes | Yes (100.00) | 7.85 |
| NT233 | T262* | Yes | Yes (96.32) | 7.1 |
| NT457 | L252K | Yes | Yes (94.48) | 8 |
| NT232 | C259A | Yes | Yes (97.24) | 7.55 |
| NT451 | E176VW237* | No | No | |

CITATIONS

Ago et al., Eur. J. Biochem. 225:369-374 (1974).
Hudak et al., J. Biol. Chem. 274:3859-3864 (1999).
Hudak et al., RNA 6:369-380 (2000).
Hudak et al., Virology 279:292-301 (2001).
Hur et al., Proc. Natl. Acad. Sci. USA 92:8448-8452 (1995).
Rajamohan et al., J. Biol. Chem. 275:3382-3390 (2000).

INDUSTRIAL APPLICABILITY

The present invention is useful in agricultural biotechnology as well as in the fields of pharmaceutics and medicine.

All patent and non-patent publications cited in this specification are indicative of the level of skill of those skilled in the art to which this invention pertains. All these publications are herein incorporated by reference to the same extent as if each individual publication was specifically and individually indicated to be incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A non-cytotoxic isolated pokeweed antiviral protein (PAP) mutant comprising PAP (1-249) which consists of amino acids 23-271 of SEQ ID NO:2, PAP (1-250) which consists of amino acids 23-272 of SEQ ID NO:2 or PAP (1-251) which consists amino acids 23-273 of SEQ ID NO:2.

2. A non-cytotoxic PAP mutant of comprising the PAP mutant of claim 1 and further comprising the N-terminal signal sequence of wild-type PAP.

3. A non-cytotoxic fusion protein comprising the PAP mutant of claim 1 and a targeting moiety that binds a cell surface receptor.

4. A non-cytotoxic immunoconjugate comprising the PAP mutant of claim 1 and a targeting moiety that binds a cell surface receptor.

5. A composition comprising a carrier and the fusion protein of claim 3 or the immunoconjugate of claim 4 or the isolated pokeweed antiviral protein (PAP) mutant of claim 1.

* * * * *

UNITED STATES PATENT AND TRADEMARK OFFICE

CERTIFICATE OF CORRECTION

PATENT NO. : 7,462,694 B2
APPLICATION NO. : 10/467009
DATED : December 9, 2008
INVENTOR(S) : Nilgun E. Tumer et al.

It is certified that error appears in the above-identified patent and that said Letters Patent is hereby corrected as shown below:

Column 35, line 25 after “consists” insert --of--.
Column 35, line 26 after “mutant” delete “of”.

Signed and Sealed this

Fourth Day of May, 2010

David J. Kappos
*Director of the United States Patent and Trademark Office*